United States Patent [19] [11] 4,205,173
Shetty [45] May 27, 1980

[54] 1-HETEROCYCLIC ALKYL-1,2,3,4-TETRAHYDROQUINAZOLINONES AND ANALGESIC INTERMEDIATES THEREOF

[75] Inventor: Bola V. Shetty, Rockville, Md.

[73] Assignee: Pennwalt Corporation, Philadelphia, Pa.

[21] Appl. No.: 716,930

[22] Filed: Aug. 23, 1976

Related U.S. Application Data

[60] Continuation-in-part of Ser. No. 452,587, Mar. 19, 1974, abandoned, which is a continuation of Ser. No. 108,659, Jan. 21, 1971, abandoned, which is a division of Ser. No. 691,955, Dec. 20, 1967, Pat. No. 3,635,976.

[51] Int. Cl.² .................................................. C07D 211/52
[52] U.S. Cl. ........................................ 546/218; 546/217; 424/267
[58] Field of Search ................... 260/293.77; 546/217, 546/218

[56] References Cited

U.S. PATENT DOCUMENTS

| | | | |
|---|---|---|---|
| 3,215,697 | 11/1965 | Hauptmann et al. | 260/256.4 F |
| 3,290,317 | 12/1966 | Carabateas | 260/293.77 |
| 3,455,935 | 7/1969 | Fancher et al. | 260/293.77 |
| 3,497,514 | 2/1970 | Okumura et al. | 260/256.4 |
| 3,635,976 | 1/1972 | Shetty | 260/256.4 F |
| 3,862,158 | 1/1975 | Edenhofer et al. | 260/293.77 |

*Primary Examiner*—Norma S. Milestone

[57] ABSTRACT

1-Heterocyclic alkyl-1,2,3,4-tetrahydroquinazolinones, acid addition salts thereof, and intermediate compounds having analgesic properties. A representative quinazolinone compound is 1-[2-(1-phenyl-4-piperazinyl)-ethyl]-2-phenyl-1,2,3,4-tetrahydro-4-quinazolinone. A representative analgesic intermediate is 2-[2-(4-[1-phenyl]-piperazinyl)ethylamino] bezamide.

4 Claims, No Drawings

1-HETEROCYCLIC ALKYL-1,2,3,4-TETRAHYDROQUINAZOLINONES AND ANALGESIC INTERMEDIATES THEREOF

The invention relates to 1-heterocyclic alkyl-1,2,3,4-tetrahydroquinazolinones, acid addition salts, and intermediate compounds thereof characterized by having analgesic properties.

More particularly the invention relates to compounds from the group consisting of A, compounds of the formula:

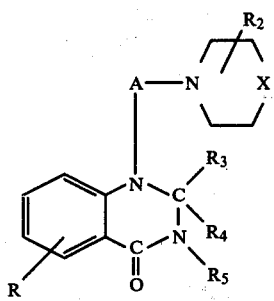

wherein X is NH, NR$_1$, CH$_2$, CHR$_1$,

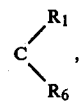

O or S; R$_6$ is OH or OCOR$_7$ where R$_7$ is loweralkyl, e.g., CH$_3$, CH$_2$—CH$_3$, CH$_2$CH$_2$CH$_3$ or

A is (CH$_2$)$_n$ where n is 1–5, or a branced alkylene with 3 to 5 carbon atoms;

R is H, loweralkyl, hydroxy, loweralkoxy, halogen, amino, or substituted amino (e.g.—NHCOCH$_3$, —NHCHO), NO$_2$;

R$_1$ is H, loweralkyl, aryl, or substituted aryl (e.g. NH$_2$, OH, OCH$_3$, CH$_3$, Cl)

R$_2$ is H, loweralkyl

R$_3$ and R$_4$ each is H, aryl, substituted aryl e.g. NH$_2$, CH$_3$CONH—, OH, OCH$_3$, CH$_3$, Cl), aralkyl, substituted aralkyl (e.g OH, NH$_2$, OCH$_3$, CH$_3$, Cl), loweralkyl, or heterocyclic, R$_3$ and R$_4$ can be joined together to form with the two position carbon atom to which they are attached, a cycloaliphatic or heterocyclic ring substituted or unsubstituted preferably having 3 to 10 carbon atoms, R$_5$ is H, loweralkyl, aryl, substituted aryl, or aralkyl;

B, compounds of the formula:

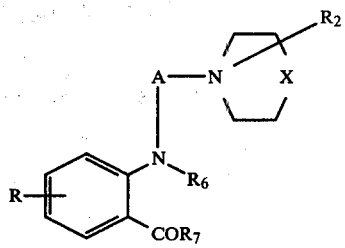

wherein X is NH, NR$_1$, CH$_2$, CHR$_1$,

where R$_8$ is OH or OCOR$_9$, and R$_9$ is loweralkyl; or O or S,

R is H, loweralkyl, hydroxy, loweralkoxy, halogen, amino, or substituted amino group (e.g NHCHO, NH—CH$_3$), NO$_2$;

A is (CH$_2$)$_n$ where n is 1-5, or a branched alkylene with 3 to 5 carbon atoms, R$_1$ is H, loweralkyl, aryl, substituted aryl (e.g. OH, OCH$_3$, NH$_2$, CH$_3$, Cl), aralkyl, or substituted aralkyl (e.g OH, OCH$_3$, NH$_2$, CH$_3$, Cl), R$_2$ is H, loweralkyl, R$_6$ is H, loweralkyl, loweralkanoyl, benzoyl, aryl, substituted aryl, aralkyl, substituted aralkyl, benzyl, substituted benzyl (e.g OH, OCH$_3$, NH$_2$, CH$_3$, Cl), or heterocyclic, R$_7$ is OH, loweralkoxy, (e.g. OCH$_3$, OCH$_2$ CH$_3$), heterocyclic

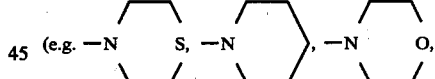
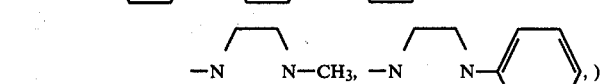
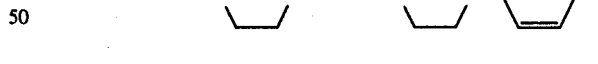

NH$_2$, —NH-loweralkyl, or —N=(disubstituted with low-eralkyl), and C pharmacologically acceptable acid addition salts of the above compounds of A and B;

the "lower" alkyl groups preferably having 1-4 carbons.

The compounds of the present invention may be prepared by various methods which are known in principle. A convenient method is illustrated in the following diagram of a general synthetic route, wherein R, R' and R" represent radicals such as shown in the formulae above. There are also given below two synthetic schemes for the preparation of specific compounds of this invention. The schematic and short hand representations are those known in the art.

GENERAL SYNTHETIC ROUTE
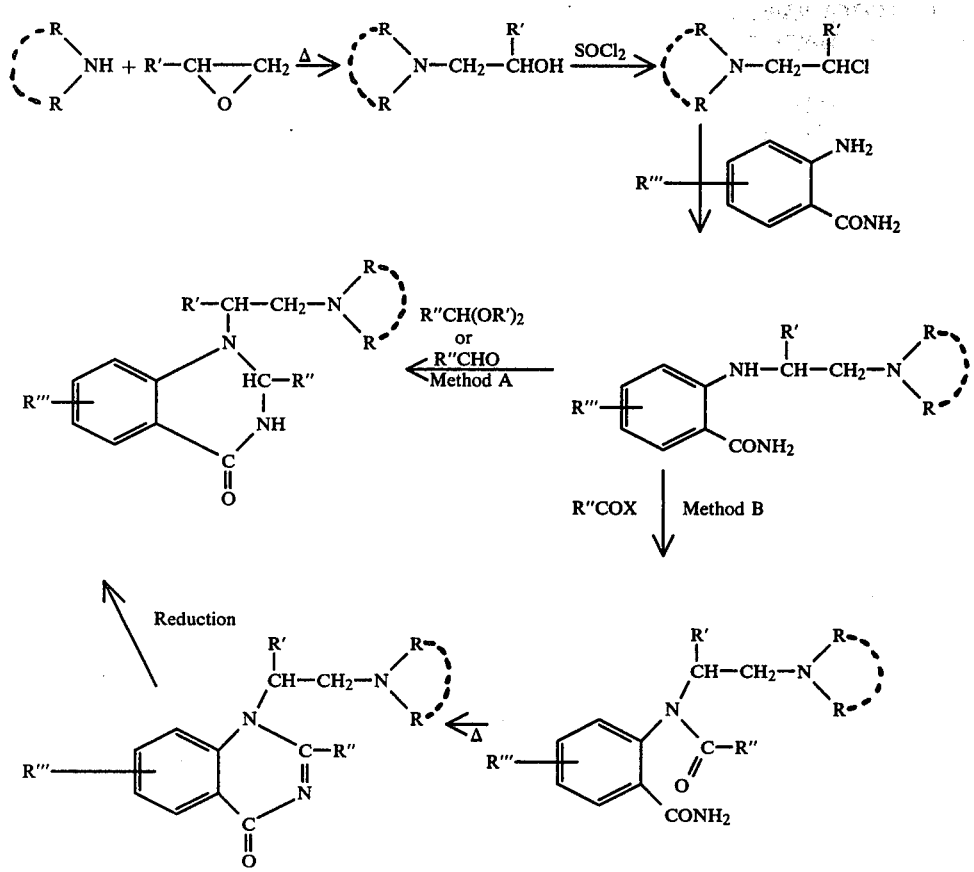
Synthetic Scheme for the Preparation of
2-[2-(4-[1-Phenyl]piperazinyl)ethylamino]-benzamide
and 1-[2-(1-Phenyl-4-piperazinyl)
ethyl]-2-phenyl-1,2,3,4-tetrahydro-4-quinazolinone
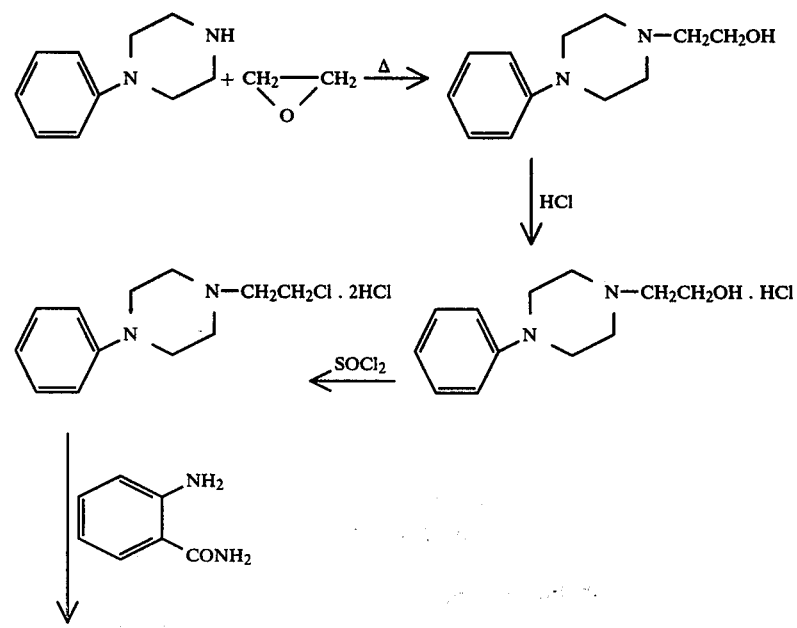

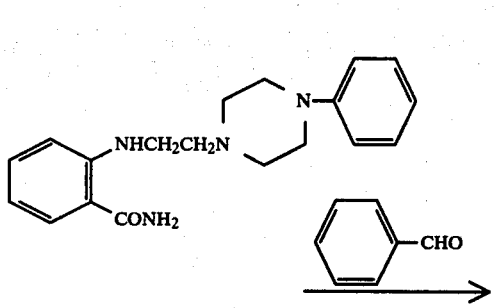
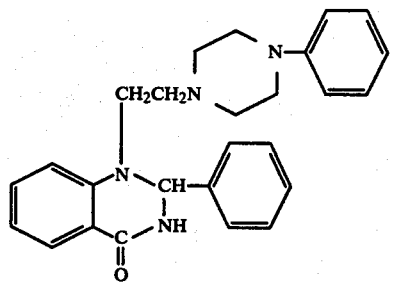

Alternate Route Force Synthesis of 1-[2-(1Phenyl-4-piperazinyl)-ethyl]-2-phenyl-1,2,3,4-tetrahydro-4-quinazolinone 2-(o-Methoxyphenyl)-1-[2-(1-Phenyl-4-piperazinyl)-ethyl]-1,2,3,4,-tetrahydro-4-quinazolinone
2-(m-Methoxyphenyl)-1-[2-(1-Phenyl-4-piperazinyl)-

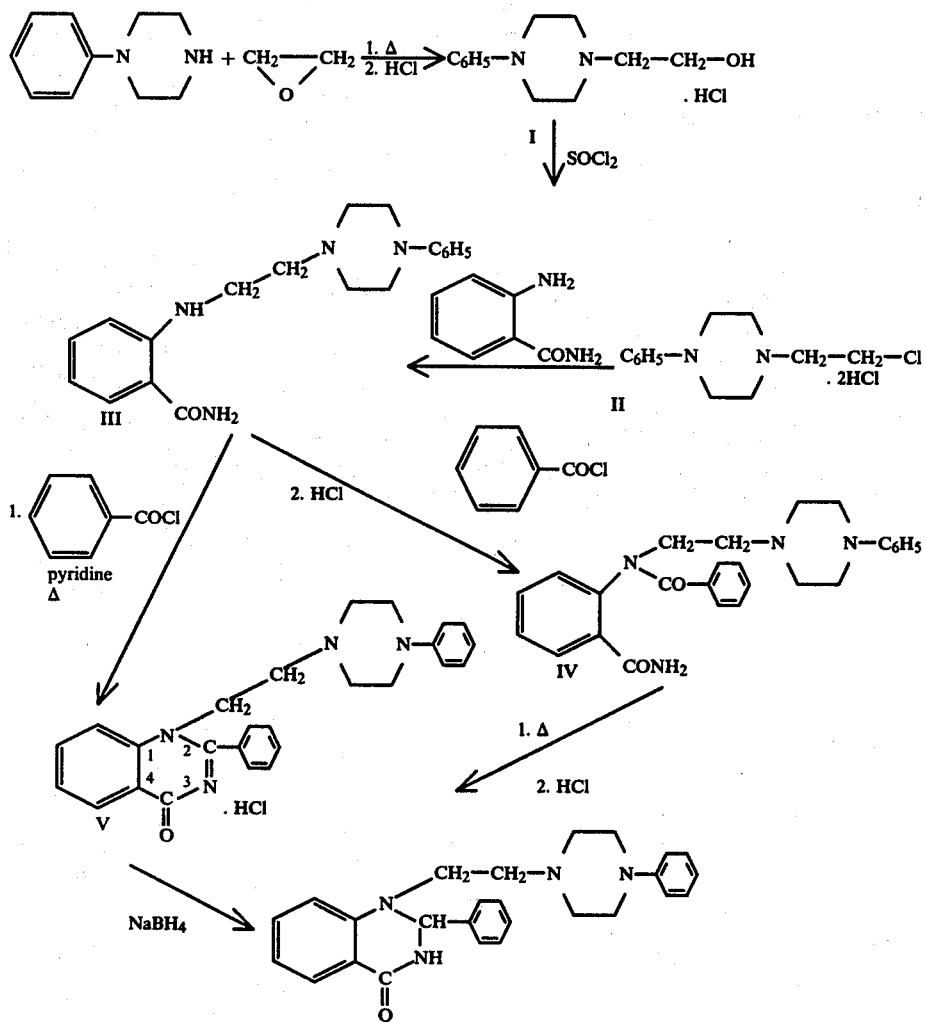

Typical examples of 1-piperazinyl-1,2,3,4-tetrahydro-4-quinazolinones which are effective analgesics for warm blooded animals are as follows:

2-(o-Aminophenyl)-1-[2-(1-Phenyl-4-piperazinyl)-ethyl]-1,2,3,4-tetrahydro-4-quinazolinone
2-(m-Aminophenyl)-1-[2-(1-Phenyl-4-piperazinyl)-ethyl]-1,2,3,4-tetrahydro-4-quinazolinone
2-(p-Aminophenyl)-1-[2-(1-Phenyl-4-piperazinyl)-ethyl]-1,2,3,4-tetrahydro-4-quinazolinone
2-(p-Methoxyphenyl)-1-[2-(1-Phenyl-4-piperazinyl)-ethyl]-1,2,3,4-tetrahydro-4-quinazolinone
2-(o-Hydroxyphenyl)-1-[2-(1-Phenyl-4-piperazinyl)-ethyl]-1,2,3,4-tetrahydro-4-quinazolinone
2-(m-Hydroxyphenyl)-1-[2-(1-Phenyl-4-piperazinyl)-ethyl]-1,2,3,4-tetrahydro-4-quinazolinone
2-(p-Hydroxyphenyl)-1-[2-(1-Phenyl-4-piperazinyl)-ethyl]-1,2,3,4-tetrahydro-4-quinazolinone 2-(o-Chlorophenyl)-1-[2-(1-Phenyl-4-piperazinyl)-ethyl]-1,2,3,4-tetrahydro-4-quinazolinone
2-(m-Chlorophenyl)-1-[2-(1-Phenyl-4-piperazinyl)-ethyl]-1,2,3,4-tetrahydro-4-quinazolinone
2-(p-Chlorophenyl)-1-[2-(1-Phenyl-4-piperazinyl)-ethyl]-1,2,3,4-tetrahydro-4-quinazolinone
2-(o-Bromophenyl)-1-[2-(1-Phenyl-4-piperazinyl)-ethyl]-1,2,3,4-tetrahydro-4-quinazolinone
2-(m-Bromophenyl)-1[2-(1-Phenyl-4-piperazinyl)-ethyl]-1,2,3,4-tetrahydro-4-quinazolinone
2-(p-Bromophenyl)-1-[2-(1-Phenyl-4-piperazinyl)-ethyl]-1,2,3,4-tetrahydro-4-quinazolione
1-[2-(1-Phenyl-4-piperazinyl)-ethyl]-2-(o-tolyl)-1,2,3,4-tetrahydro-4-quinazolinone
1-[2-(1-Phenyl-4-piperazinyl)-ethyl]-2-(m-tolyl)-1,2,3,4-tetrahydro-4-quinazolinone
1 [2-(1-Phenyl-4-piperazinyl)-ethyl]-2-(p-tolyl)-1,2,3,4-tetrahydro-4-quinazolinone
2-Cyclohexyl-1-[2-(1-phenyl-4-piperazinyl)-ethyl]-1,2,3,4-tetrahydro-4-quinazolinone
2-(o-Carboxyphenyl)-1-[2-(1-phenyl-4-piperazinyl)-ethyl]-1,2,3,4-tetrahydro-4-quinazolinone
2-(m-Carboxyphenyl)-1-[2-(1-phenyl-4-piperazinyl)-ethyl]-1,2,3,4-tetrahydro-4-quinazolinone
2-(p-Carboxyphenyl)-1-[2-(1-phenyl-4-piperazinyl)-ethyl]-1,2,3,4-tetrahydro-4-quinazolinone
2-(o-Carbomethoxyphenyl)-1-[2-(1-phenyl-4-piperazinyl)-ethyl]-1,2,3,4-tetrahydro-4-quinazolinone
2-(m-Carbomethoxyphenyl)-1-[2-(1-phenyl-4-piperazinyl)-ethyl]-1,2,3,4-tetrahydro-4-quinazolinone
2-(p-Carbomethoxyphenyl)-1-[2-(1-phenyl-4-piperazinyl)-ethyl]-1,2,3,4-tetrahydro-4-quinazolinone
1-[2-(1-Phenyl-4-piperazinyl)-ethyl]-2-(2-pyridyl)-1,2,3,4-tetrahydro-4-quinazolinone
1-[2-(1-Phenyl-4-piperazinyl)-ethyl]-2-(3-pyridyl)-1,2,3,4-tetrahydro-4-quinazolinone
1-[2-(1-Phenyl-4-piperazinyl)-ethyl]-2-(4-pyridyl)-1,2,3,4-tetrahydro-4-quinazolinone
1-[2-(1-Phenyl-4-piperazinyl)-ethyl]-2-(2-pyridylmethyl)-1,2,3,4-tetrahydro-4-quinazolinone
1-[2-(1-Phenyl-4-piperazinyl)-ethyl]-2-(3-pyridylmethyl)-1,2,3,4-tetrahydro-4-quinazolinone
1-[2-(1-Phenyl-4-piperazinyl)-ethyl]-2-(4-pyridylmethyl)-1,2,3,4-tetrahydro-4-quinazolinone
2-Morpholinyl-1-[2-(1-phenyl-4-piperazinyl)-ethyl]-1,2,3,4-tetrahydro-4-quinazolinone
2-Benzyl-1-[2-(1-phenyl-4-piperazinyl)-ethyl]-1,2,3,4-tetrahydro-4-quinazolinone
2-(o-Aminobenzyl)-1-[2-(1-phenyl-4-piperazinyl)-ethyl]-1,2,3,4-tetrahydro-4quinazolinone
2-(m-Aminobenzyl)-1-[2-(1-phenyl-4-piperazinyl)-ethyl]-1,2,3,4-tetrahydro-4-quinazolinone
2-(p-Aminobenzyl)-1-[2-(1-phenyl-4-piperazinyl)-ethyl]-1,2,3,4-tetrahydro-4-quinazolinone
2-(o-Methyoxybenzyl)-1-[2-(1-phenyl-4-piperazinyl)-ethyl]-1,2,3,4-tetrahydro-4-quinazolinone
2-(m-Methoxybenzyl)-1-[2-(1-phenyl-4-piperazinyl)-ethyl]-1,2,3,4-tetrahydro-4-quinazolinone
2-(p-Methoxybenzyl)-1-[2-(1-phenyl-4-piperazinyl)-ethyl]-1,2,3,4-tetrahydro-4-quinazolinone
2-(o-Hydroxybenzyl)-1-[2-(1-phenyl-4-piperazinyl)-ethyl]-1,2,3,4- tetrahydro-4-quinazolinone
2-(m-Hydroxybenzyl)-1-[2-(1-phenyl-4-piperazinyl)-ethyl]-1,2,3,4-tetrahydro-4-quinazolinone
2-(p-Hydroxybenzyl)-1-[2-(1-phenyl-4-piperazinyl)-ethyl]-1,2,3,4-tetrahydro-4-quinazolinone
1-[2-(1-phenyl-4-piperazinyl)-ethyl]-1,2,3,4-tetrahydro-4-quinazolinone
2-Methyl-1-[2-(1-phenyl-4-piperazinyl)-ethyl]-1,2,3,4-tetrahydro-4-quinazolinone
2-Ethyl-1-[2-(1-phenyl-4-piperazinyl)-ethyl]-1,2,3,4-tetrahydro-4-quinazolinone
1-[2-(1-phenyl-4-piperazinyl)-ethyl]-2-propyl-1,2,3,4-tetrahydro-4-quinazolinone
2,2-Dimethyl-1-[2-(1-phenyl-4-piperazinyl)-ethyl]-1,2,3,4-tetrahydro-4-quinazolinone
1'-[2-(1-phenyl-4-piperazinyl)-ethyl]spiro(cyclopentane-1,2'(1'H)-quinazolin)-4'(3'H)-one
1'-[2-(1-phenyl-4-piperazinyl)-ethyl]spiro(cyclohexane-1,2'(1'H)-quinazolin)-4'(3'H)-one
1-Methyl-1'-[2-(1-phenyl-4-piperazinyl)-ethyl]spiro[piperidine-4,2'(1'H)-quinazolin]-4'(3'H)-one
5-Amino-2-phenyl-1-[2-(1-phenyl-4-piperazinyl)-ethyl]-1,2,3,4-tetrahydro-4-quinazolinone
6-Amino-2-phenyl-1-[2-(1-phenyl-4-piperazinyl)-ethyl]-1,2,3,4-tetrahydro-4-quinazolinone
7-Amino-2-phenyl-1-[2-(1-phenyl-4-piperazinyl)-ethyl]-1,2,3,4-tetrahydro-4-quinazolinone
8-Amino-2-phenyl-1-[2-(1-phenyl-4-piperazinyl)-ethyl]-1,2,3,4-tetrahydro-4-quinazolinone
5-Methoxy-2-phenyl-1-[2-(1-phenyl-4-piperazinyl)-ethyl]-1,2,3,4-tetrahydro-4-quinazolinone
6-Methoxy-2-phenyl-1-[2-(1-phenyl-4-piperazinyl)-ethyl]-1,2,3,4-tetrahydro-4-quinazolinone
7-Methoxy-2-phenyl-1-[2-(1-phenyl-4-piperazinyl)-ethyl]-1,2,3,4-tetrahydro-4-quinazolinone
8-Methoxy-2-phenyl-1-[2-(1-phenyl-4-piperazinyl)-ethyl]-1,2,3,4-tetrahydro-4-quinazolinone
5-Hydroxy-2-phenyl-1-[2-(1-phenyl-4-piperazinyl)-ethyl]-1,2,3,4-tetrahydro-4-quinazolinone
6-Hydroxy-2-phenyl-1-[2-(1-phenyl-4-piperazinyl)-ethyl]-1,2,3,4-tetrahydro-4-quinazolinone
7-Hydroxy-2-phenyl-1-[2-(1-phenyl-4-piperazinyl)-ethyl]-1,2,3,4-tetrahydro-4-quinazolinone
8-Hydroxy-2-phenyl-1-[2-(1-phenyl-4-piperazinyl)-ethyl]-1,2,3,4-tetrahydro-4-quinazolinone
5-Chloro-2-phenyl-1-[2-(1-phenyl-4-piperazinyl)-ethyl]-1,2,3,4-tetrahydro-4-quinazolinone
6-Chloro-2-phenyl-1-[2-(1-phenyl-4-piperazinyl)-ethyl]-1,2,3,4-tetrahydro-4-quinazolinone
7-Chloro-2-phenyl-1-[2-(1-phenyl-4-piperazinyl)-ethyl]-1,2,3,4-tetrahydro-4-quinazolinone
8-Chloro-2-phenyl-1-[2-(1-phenyl-4-piperazinyl)-ethyl]-1,2,3,4-tetrahydro-4-quinazolinone
5-Methyl-2-phenyl-1-[2-(1-phenyl-4-piperazinyl)-ethyl]-1,2,3,4-tetrahydro-4-quinazolinone
6-Methyl-2-phenyl-1-[2-(1-phenyl-4-piperazinyl)-ethyl]-1,2,3,4-tetrahydro-4-quinazolinone
7-Methyl-2-phenyl-1-[2-(1-phenyl-4-piperazinyl)-ethyl]-1,2,3,4-tetrahydro-4-quinazolinone
8-Methyl-2-phenyl-1-[2-(1-phenyl-4-piperazinyl)-ethyl]-1,2,3,4-tetrahydro4-quinazolinone
5-Formamido-2-phenyl-1-[2-(1-phenyl-4-piperazinyl)-ethyl]-1,2,3,4-tetrahydro-4-quinazolinone
6-Formamido-2-phenyl-1-[2-(1-phenyl-4-piperazinyl)-ethyl]-1,2,3,4-tetrahydro-4-quinazolinone
7-Formamido-2-phenyl-1-[2-(1-phenyl-4-piperazinyl)-ethyl]-1,2,3,4-tetrahydro-4-quinazolinone 8-Formamido-2-phenyl-1-[2-(1-phenyl-4-piperazinyl)-ethyl]-1,2,3,4-tetrahydro-4-quinazolinone
2-Phenyl-1-[2-(1-phenyl-4-piperazinyl)-ethyl]-6-trifluoromethyl-1,2,3,4-tetrahydro-4-quinazolinone
2-Phenyl-1-[2-(1-phenyl-4-piperazinyl)-ethyl]-7-trifluoromethyl-1,2,3,4-tetrahydro-4-quinazolinone
2-Phenyl-1-[2-(1-phenyl-4-piperazinyl)-ethyl]-1,2,3,4-tetrahydro-4-quinazolinone
2-Phenyl-1-[3-(1-phenyl-4-piperazinyl)-propyl]-1,2,3,4-tetrahydro-4-quinazolinone
1-[1-Methyl-2-(1-phenyl-4-piperazinyl)-ethyl]-2-phenyl-1,2,3,4-tetrahydro-quinazolinone
d-1-[1-Methyl-2-(1-phenyl-4-piperazinyl)-ethyl]-2-phenyl-1,2,3,4-tetrahydro-4-quinazolinone
l-1[1-Methyl-2-(1-phenyl-4-piperazinyl)-ethyl]-2-phenyl-1,2,3,4-tetrahydro-4-quinazolinone
1-[2-Methyl-2-(1-phenyl-4-piperazinyl)-ethyl]-2-phenyl-1,2,3,4-tetrahydro-4-quinazolinone
d-1-[2-Methyl-2-(1-phenyl-4-piperazinyl)-ethyl]-2-phenyl-1,2,3,4-tetrahydro-4-quinazolinone
l-1-[2-Methyl-2-(1-phenyl-4-piperazinyl)-ethyl]-2-phenyl-1,2,3,4-tetrahydro-4-quinazolinone
1-[2-(1-[o-Chlorophenyl]-4-piperazinyl)-ethyl]-2-phenyl-1,2,3,4-tetrahydro-4-quinazolinone
1-[2-(1-[m-Chlorophenyl]-4-piperazinyl)-ethyl]-2-phenyl-1,2,3,4-tetrahydro-4-quinazolinone
1-[2-(1-[p-Chlorophenyl]-4-piperazinyl)-ethyl]-2-phenyl-1,2,3,4-tetrahydro-4-quinazolinone
1-[2-(1-[o-Aminophenyl]-4-piperazinyl)-ethyl]-2-phenyl-1,2,3,4-tetrahydro-4-quinazolinone
1-[2-(1-[m-Aminophenyl]-4-piperazinyl)-ethyl]-2-phenyl-1,2,3,4,-tetrahydro-4-quinazolinone
1-[2-(1-[p-Aminophenyl]-4-piperazinyl)-ethyl]-2-phenyl-1,2,3,4-tetrahydro-4-quinazolinone
1-[2-(1-[o-Methoxyphenyl]-4-piperazinyl)-ethyl]-2-phenyl-1,2,3,4-tetrahydro-4-quinazolinone
1-[2-(1-[m-Methoxyphenyl]-4-piperazinyl)-ethyl]-2-phenyl-1,2,3,4-tetrahydro-4-quinazolinone
1-[2-(1-[p-Methoxyphenyl]-4-piperazinyl)-ethyl]-2-phenyl-1,2,3,4-tetrahydro-4-quinazolinone
1-[2-(1-[o-Hydroxyphenyl]-4-piperazinyl)-ethyl]-2-phenyl-1,2,3,4-tetrahydro-4-quinazolinone
1-[2-(1-[m-Hydroxyphenyl]-4-piperazinyl)-ethyl]-2-phenyl-1,2,3,4-tetrahydro-4-quinazolinone
1-[2-(1-[p-Hydroxyphenyl]-4-piperazinyl)-ethyl]-2-phenyl-1,2,3,4-tetrahydro-4-quinazolinone
2-Phenyl-1-[2-(1-[o-tolyl]-4-piperazinyl)-ethyl]-1,2,3,4-tetrahydro-4-quinazolinone
2-Phenyl-1-[2-(1-[m-tolyl]-4-piperazinyl)-ethyl]-1,2,3,4-tetrahydro-4-quinazolinone
2-Phenyl-1-[2-(1-[p-tolyl]-4-piperazinyl)-ethyl]-1,2,3,4-tetrahydro-4-quinazolinone
1-[3-(1-[o-Chlorophenyl]-4-piperazinyl)-propyl]-2-phenyl-1,2,3,4-tetrahydro-4-quinazolinone
1-[3-(1-[m-Chlorophenyl]-4-piperazinyl)-propyl]-2-phenyl-1,2,3,4-tetrahydro-4-quinazolinone
1-[3-(1-[p-Chlorophenyl]-4-piperazinyl)-propyl]-2-phenyl-1,2,3,4-tetrahydro-4-quinazolinone
1-[3-(1-[o-Aminophenyl]-4-piperazinyl)-propyl]-2-phenyl-1,2,3,4-tetrahydro-4-quinazolinone
1-[3-(1-[m-Aminophenyl]-4-piperazinyl)-propyl]-2-phenyl-1,2,3,4-tetrahydro-4-quinazolinone
1-[3-(1-[p-Aminophenyl]-4-piperazinyl)-propyl]-2-phenyl-1,2,3,4-tetrahydro-4-quinazolinone
1-[3-(1-[o-Methoxyphenyl]-4-piperazinyl)-propyl]-2-phenyl-1,2,3,4-tetrahydro-4-quinazolinone
1-[3-(1-[m-Methoxyphenyl]-4-piperazinyl)-propyl]-2-phenyl-1,2,3,4-tetrahydro-4-quinazolinone
1-[3-(1-[p-Methoxyphenyl]-4-piperazinyl)-propyl]-2-phenyl-1,2,3,4-tetrahydro-4-quinazolinone
1-[3-(1-[o-Hydroxyphenyl]-4-piperazinyl)-propyl]-2-phenyl-1,2,3,4-tetrahydro-4-quinazolinone
1-[3-(1-[m-Hydroxyphenyl]-4-piperazinyl)-propyl]-2-phenyl-1,2,3,4-tetrahydro-4-quinazolinone
1-[3-(1-[p-Hydroxyphenyl]-4-piperazinyl)-propyl]-2-phenyl-1,2,3,4-tetrahydro-4-quinazolinone
2-Phenyl-1-[3-(1-[o-tolyl]-4-piperazinyl)-propyl]-1,2,3,4-tetrahydro-4-quinazolinone
2-Phenyl-1-[3-(1-[m-tolyl]-4-piperazinyl)-propyl]-1,2,3,4-tetrahydro-4-quinazolinone
2-Phenyl-1-[3-(1-[p-tolyl]-4-piperazinyl)-propyl]-1,2,3,4-tetrahydro-4-quinazolinone
1-[1-Methyl-2-(1-[o-chlorophenyl]-4-piperazinyl)-ethyl]-2-phenyl-1,2,3,4-tetrahydro-4-quinazolinone
d-1-[1-Methyl-2-(1-[o-chlorophenyl]-4-piperazinyl)-ethyl]-2-phenyl-1,2,3,4-tetrahydro-4-quinazolinone
l-1-[1-Methyl-2-(1-[o-clorophenyl]-4-piperazinyl)-ethyl]-2-phenyl-1,2,3,4-tetrahydro-4-quinazolinone
1-[1-Methyl-2-(1-[m-chlorophenyl]-4-piperazinyl)-ethyl]-2-phenyl-1,2,3,4-tetrahydro-4-quinazolinone
d-1-[1-Methyl-2-(1-[m-chlorophenyl]-4-piperazinyl)-ethyl]-2-phenyl-1,2,3,4-tetrahydro-4-quinazolinone
l-1-[1-Methyl-2-(1-[m-chlorophenyl]-4-piperazinyl)-ethyl]-2-phenyl-1,2,3,4-tetrahydro-4-quinazolinone
1-[1-Methyl-2-(1-[p-chlorophenyl]-4-piperazinyl)-ethyl]-2-phenyl-1,2,3,4-tetrahydro-4-quinazolinone
d-1-[1-Methyl-2-(1-[p-chlorophenyl]-4-piperazinyl)-ethyl]-2-phenyl-1,2,3,4-tetrahydro-4-quinazolinone
l-1-[1-Methyl-2-(1-[p-chlorophenyl]-4-piperazinyl)-ethyl]-2-phenyl-1,2,3,4-tetrahydro-4-quinazolinone
1-[1-Methyl-2-(1-[o-aminophenyl]-4-piperazinyl)-ethyl]-2-phenyl-1,2,3,4-tetrahydro-4-quinazolinone
d-1-[1-Methyl-2-(1-[o-aminophenyl]-4-piperazinyl)-ethyl]-2-phenyl-1,2,3,4-tetrahydro-4-quinazolinone
l-1-[1-Methyl-2-(1-[o-aminophenyl]-4-piperazinyl)-ethyl]-2-phenyl-1,2,3,4-tetrahydro-4-quinazolinone
1-[1-Methyl-2-(1[m-aminophenyl]-4-piperazinyl)-ethyl]-2-phenyl-1,2,3,4-tetrahydro-4-quinazolinone
d-1-[1-Methyl-2-(1-[m-aminophenyl]-4-piperazinyl)-ethyl]-2-phenyl-1,2,3,4-tetrahydro-4-quinazolinone
l-1-[1-Methyl-2-(1-[m-aminophenyl]-4-piperazinyl)-ethyl]-2-phenyl-1,2,3,4-tetrahydro-4-quinazolinone
1-[1-Methyl-2-(1-[p-aminophenyl]-4-piperazinyl)-ethyl]-2-phenyl-1,2,3,4-tetrahydro-4-quinazolinone
d-1-[1-Methyl-2-(1-[p-aminophenyl]-4-piperazinyl)-ethyl]-2-phenyl-1,2,3,4-tetrahydro-4-quinazolinone
l-1-[1-Methyl-2-(1-[p-aminophenyl]-4-piperazinyl)-ethyl]-2-phenyl-1,2,3,4-tetrahydro-4-quinazolinone
1-[1-Methyl-2-(1-[o-methoxyphenyl]-4-piperazinyl)-ethyl]-2-phenyl-1,2,3,4-tetrahydro-4-quinazolinone
d-1-[1-Methyl-2-(1-[o-methoxyphenyl]-4-piperazinyl)-ethyl-2-phenyl-1,2,3,4-tetrahydro-4-quinazolinone
l-1-[1-Methyl-2-(1-[o-methoxyphenyl]-4-piperazinyl)-ethyl]-2-phenyl-1,2,3,4-tetrahydro-4-quinazolinone
1-[1-Methyl-2-(1-[m-methoxyphenyl]-4-piperazinyl)-ethyl]-2-phenyl-1,2,3,4-tetrahydro-4-quinazolinone
d-1-[1-Methyl-2-(1-[m-methoxyphenyl]-4-piperazinyl)-ethyl]-2-phenyl-1,2,3,4-tetrahydro-4-quinazolinone
l-1-[1-Methyl-2-(1-[m-methoxyphenyl]-4-piperazinyl)-ethyl]-2-phenyl-1,2,3,4-tetrahydro-4-quinazolinone 1-[1-Methyl-2-(1-[p-methoxyphenyl]-4-piperazinyl)-ethyl]-2-phenyl-1,2,3,4-tetrahydro-4-quinazolinone
d-1-[1-Methyl-2-(1-[p-methoxyphenyl]-4-piperazinyl)-ethyl]-2-phenyl-1,2,3,4-tetrahydro-4-quinazolinone
1-1-[1-Methyl-2-(1-[p-methoxyphenyl]-4-piperazinyl)-ethyl]-2-phenyl-1,2,3,4-tetrahydro-4-quinazolinone
1-[1-Methyl-2-(1-[o-hydroxyphenyl]-4-piperazinyl)-ethyl]-2-phenyl-1,2,3,4-tetrahydro-4-quinazolinone
d-1-[1-Methyl-2-(1-[o-hydroxyphenyl]-4-piperazinyl)-ethyl]-2-phenyl-1,2,3,4-tetrahydro-4-quinazolinone
1-1-[1-Methyl-2-(1-[o-hydroxyphenyl]-4-piperazinyl)-ethyl]-2-phenyl-1,2,3,4-tetrahydro-4-quinazolinone
1-[1-Methyl-2-(1-[m-hydroxyphenyl]-4-piperazinyl)-ethyl]-2-phenyl-1,2,3,4-tetrahydro-4-quinazolinone
d-1-[1-Methyl-2-(1-[m-hydroxyphenyl]-4-piperazinyl)-ethyl]-2-phenyl-1,2,3,4-tetrahydro-4-quinazolinone
1-1-[1-Methyl-2-(1-[m-hydroxyphenyl]-4-piperazinyl)-ethyl]-2-phenyl-1,2,3,4-tetrahydro-4-quinazolinone
1-[1-Methyl-2-(1-[p-hydroxyphenyl]-4-piperazinyl)-ethyl]-2-phenyl-1,2,3,4-tetrahydro-4-quinazolinone
d-1-[1-Methyl-2-(1-[p-hydroxyphenyl]-4-piperazinyl)-ethyl]-2-phenyl-1,2,3,4-tetrahydro-4-quinazolinone
1-1-[1-Methyl-2-(1-[p-hydroxyphenyl]-4-piperazinyl)-ethyl]-2-phenyl-1,2,3,4-tetrahydro-4-quinazolinone
1-[1-Methyl-2-(1-[o-tolyl]-4-piperazinyl)-ethyl]-2-phenyl-1,2,3,4-tetrahydro-4-quinazolinone
d-1-[1-Methyl-2-(1-[o-tolyl]-4-piperazinyl)-ethyl]-2-phenyl-1,2,3,4-tetrahydro-4-quinazolinone
1-1-[1-Methyl-2-(1-[o-tolyl]-4-piperazinyl)-ethyl]-2-phenyl-1,2,3,4-tetrahydro-4-quinazolinone
1-[1-Methyl-2-(1-[m-tolyl]-4-piperazinyl)-ethyl]-2-phenyl-1,2,3,4-tetrahydro-4-quinazolinone
d-1-[1-Methyl-2-(1-[m-tolyl]-4-piperazinyl)-ethyl]-2-phenyl-1,2,3,4-tetrahydro-4-quinazolinone
1-1-[1-Methyl-2-(1-[m-tolyl]-4-piperazinyl)-ethyl]-2-phenyl-1,2,3,4-tetrahydro-4-quinazolinone
1-[1-Methyl-2-(1-[p-tolyl]4-piperazinyl)-ethyl]-2-phenyl-1,2,3,4-tetrahydro-4-quinazolinone
d-1-[1-Methyl-2-(1-[p-tolyl]-4-piperazinyl)-ethyl]-2-phenyl-1,2,3,4-tetrahydro-4-quinazolinone
1-1-[1-Methyl-2-(1-[p-tolyl]-4-piperazinyl)-ethyl]-2-phenyl-1,2,3,4-tetrahydro-4-quinazolinone
1-[2-Methyl-2-(1-[o-chlorophenyl]4-piperazinyl)-ethyl]-2-phenyl-1,2,3,4-tetrahydro-4-quinazolinone
d-1-[2-Methyl-2-(1-[o-chlorophenyl]-4-piperazinyl)-ethyl]-2-phenyl-1,2,3,4-tetrahydro-4-quinazolinone
1-1-[2-Methyl-2-(1-[o-chlorophenyl]-4-piperazinyl)-ethyl]-2-phenyl-1,2,3,4-tetrahydro- 4-quinazolinone
1-[2-Methyl-2-(1-[m-chlorophenyl]-4-piperazinyl)-ethyl]-2-phenyl-1,2,3,4-tetrahydro-4-quinazolinone
d-1-[2-Methyl-2-(1-[m-chlorophenyl]-4-piperazinyl)-ethyl]-2-phenyl-1,2,3,4-tetrahydro-4-quinazolinone
1-1-[2-Methyl-2-(1-[m-chlorophenyl]-4-piperazinyl-ethyl]-2-phenyl-1,2,3,4-tetrahydro-4-quinazolinone
1-[2-Methyl-2-(1-[p-chlorophenyl]-4-piperazinyl)-ethyl]-2-phenyl-1,2,3,4-tetrahydro-4-quinazolinone
d-1-[2-Methyl-2-(1[p-chlorophenyl]-4-piperazinyl)-ethyl]-2-phenyl-1,2,3,4-tetrahydro-4-quinazolinone
1-1-[2-Methyl-2-(1-[p-chlorophenyl]4-piperazinyl)-ethyl]-2-phenyl-1,2,3,4-tetrahydro-4-quinazolinone
1-[2-Methyl-2-(1-[o-aminophenyl]-4-piperazinyl)-ethyl]-2-phenyl-1,2,3,4-tetrahydro-4-quinazolinone
d-1-[2-methyl-2-(1-[o-aminophenyl]-4-piperazinyl)-ethyl]-2-phenyl-1,2,3,4-tetrahydro-4-quinazolinone
1-1-[2-Methyl-2-(1-[o-aminophenyl]-4-piperazinyl)-ethyl]-2-phenyl-1,2,3,4-tetrahydro-4-quinazolinone
1-[2-Methyl-2-(1-[m-aminophenyl]-4-piperazinyl)-ethyl]-2-phenyl-1,2,3,4-tetrahydro-4-quinazolinone
d-1-[2-Methyl-2-(1-[m-aminophenyl]-4-piperazinyl)-ethyl]-2-phenyl-1,2,3,4-tetrahydro-4-quinazolinone
1-1-[2-Methyl-2-(1-[m-aminophenyl]-4-piperazinyl)-ethyl]-2-phenyl-1,2,3,4-tetrahydro-4-quinazolinone
1-[2-Methyl-2-(1-[p-aminophenyl]-4-piperazinyl)-ethyl]-2-phenyl-1,2,3,4-tetrahydro-4-quinazolinone
d-1-[2-Methyl-2-(1-[p-aminophenyl]-4-piperazinyl)-ethyl]-2-phenyl-1,2,3,4-tetrahydro-4-quinazolinone
1-1-[2-Methyl-2-(1-[p-aminophenyl]-4-piperazinyl)-ethyl]-2-phenyl-1,2,3,4-tetrahydro-4-quinazolinone
1-[2-Methyl-2-(1-]o-methoxyphenyl]-4-piperazinyl)-ethyl]-2-phenyl-1,2,3,4-tetrahydro-4-quinazolinone
d-1-[2-Methyl-2-(1-]o-methoxyphenyl]-4-piperazinyl)-ethyl]-2-phenyl-1,2,3,4-tetrahydro-4-quinazolinone
1-1-[2-Methyl-2-(1-[o-methoxyphenyl]-4-piperazinyl)-ethyl]-2-phenyl-1,2,3,4-tetrahydro-4-quinazolinone
1-[2-Methyl-2-(1-[m-methoxyphenyl]-4-piperazinyl)-ethyl]-2-phenyl-1,2,3,4-tetrahydro-4-quinazolinone
d-1-[2-Methyl-2-(1-[m-methoxyphenyl]-4-pierazinyl)-ethyl]-2-phenyl-1,2,3,4-tetrahydro-4-quinazolinone
1-1-[2-Methyl-2 -(1-[m-methoxyphenyl]-4-piperazinyl)-ethyl]-2 -phenyl-1,2,3,4-tetrahydro-4-quinazolinone
1-[2-Methyl-2-(1-[p-methoxyphenyl]-4-piperazinyl)-ethyl]-2-phenyl-1,2,3,4-tetrahydro-4-quinazolinone
d-1-[2-Methyl-2-(1-[p-methoxyphenyl]-4-piperazinyl)-ethyl]-2-phenyl-1,2,3,4-tetrahydro-4-quinazolinone
1-1-[2-Methyl-2-(1[p-methoxyphenyl]-4-piperazinyl)-ethyl]-2-phenyl-1,2,3,4-tetrahydro-4-quinazolinone
1-[2-Methyl-2-(1-[o-hydroxyphenyl]-4-piperazinyl)-ethyl]-2-phenyl-1,2,3,4-tetrahydro-4-quinazolinone
d-1-[2-Methyl-2-(1-[o-hydroxyphenyl]-4-piperazinyl)-ethyl]-2-phenyl-1,2,3,4-tetrahydro-4-quinazolinone
1-1-[2-Methyl-2-(1-[o-hydroxyphenyl]-4-piperazinyl)-ethyl[-2-phenyl-1,2,3,4-tetrahydro-4-quinazolinone
1-[2-Methyl-2-(1-[m-hydroxyphenyl]-4-piperazinyl)-ethyl]-2-phenyl-1,2,3,4-tetrahydro-4-quinazolinone
d-1-[2-Methyl-2-(1-[m-hydroxyphenyl]-4piperazinyl)-ethyl]-2-phenyl-1,2,3,4-tetrahydro-4-quinazolinone
1-1-[2-Methyl-2-(1-[m-hydroxyphenyl]-4-piperazinyl)-ethyl]-2-phenyl-1,2,3,4-tetrahydro-4-quinazolinone
1-[2-Methyl-2-(1[p-hydroxyphenyl]-4-piperazinyl)-ethyl]-2-phenyl-1,2,3,4-tetrahydro-4-quinazolinone
d-1-[2-Methyl-2-(1-[p-hydrozyphenyl]-4-piperazinyl)-ethyl]-2-phenyl-1,2,3,4-tetrahydro-4-quinazolinone
1-1-[2-Methyl-2-(1-[p-hydroxyphenyl]-4-piperazinyl)-ethyl]-2-phenyl-1,2,3,4-tetrahydro-4-quinazolinone
1[2-Methyl-2-(1[o-tolyl]-4-piperazinyl)-ethyl]-2-phenyl-1,2,3,4-tetrahydro-4-quinazolinone d-1-[2-Methyl-2-(1-[o-tolyl]-4-piperazinyl)-ethyl]2-phenyl-1,2,3,4-tetrahydro-4-quinazolinone
l-1-[2-Methyl-2-(1-[o-toly]-4-piperazinyl)-ethyl]-2-phenyl-1,2,3,4-tetrahydro-4-quinazolinone
1-[2-Methyl-2-(1-[m-tolyl]-4-piperazinyl)-ethyl]2-phenyl-1,2,3,4-tetrahydro-4-quinazolinone
d-1-[2-Methyl-2-(1-[m-tolyl]-4-piperazinyl)-ethyl]-2-phenyl-1,2,3,4-tetrahydro-4-quinazolinone
l-1-[2-Methyl-2-(1-[m-tolyl]-4-piperazinyl)-ethyl]-2--phenyl-1,2,3,4-tetrahydro-4-quinazolinone
1-[2-Methyl-2 -(1-[p-tolyl]-4-piperazinyl)-ethyl]-2-phenyl-1,2,3,4-tetrahydro-4-quinazolinone
d-1-[2-Methyl-2-(1-[p-tolyl]-4-piperazinyl)-ethyl]-2-phenyl-1,2,3,4-tetrahydro-4-quinazolinone
l-1-[2-Methyl-2-(1-[p-tolyl]-4-piperazinyl)-ethyl]-2-phenyl-1,2,3,4-tetrahydro-4-quinazolinone
2-Phenyl-1-[2-(1-phenyl-2-methyl-4-piperazinyl)-ethyl]-1,2,3,4-tetrahydro-4-quinazolinone
2-Benzyl-1-[1-methyl-2-(1-phenyl-4-piperazinyl)-ethyl]-1,2,3,4-tetrahydro-4-quinazolinone
2-Benzyl-1-[2-(1-[p-hydroxyphenyl]-4-piperazinyl)-ethyl]-1,2,3,4-tetrahydro-4-quinazolinone
2-Benzyl-1-[2-(1-[p-methoxyphenyl]-4-piperazinyl)-ethyl]-1,2,3,4-tetrahydro-4-quinazolinone
6-Amino-2-benzyl-1-[2-(1-phenyl-4-piperazinyl)-ethyl]1,2,3,4-tetrahydro-4-quinazolinone
6-Amino-1-[2-(1-phenyl-4-piperazinyl)-ethyl]2-(2-pyridylmethyl)-1,2,3,4-tetrahydro-4-quinazolinone
6-Amino-1-[1-methyl-2-(1-phenyl-4-piperazinyl)-ethyl]-2-(2-pyridylmethyl) -1,2,3,4-tetrahydro-4-quinazolinone
3-Methyl-2-phenyl-1-[2-(1-phenyl-4-piperazinyl)-ethyl]-1,2,3,4-tetrahydro-4-quinazolinone
2-Phenyl-1-[2-(1-piperazinyl)-ethyl]-1,2,3,4-tetrahydro-4-quinazolinone
1-[2-(1-Methyl-4-piperazinyl-ethyl]-2-phenyl-1,2,3,4-tetrahydro-4-quinazolinone
1-[2-(1-Benzyl-4-piperazinyl)-ethyl]-2-phenyl-1,2,3,4-tetrahydro-4-quinazolinone
1-[2-(1-Phenethyl-4-piperazinyl)-ethyl]-2-phenyl-1,2,3,4-tetrahydro-4-quinazolinone
1-[2-(1-[p-aminophenethyl]-4-piperazinyl)-ethyl]-2-phenyl-1,2,3,4-tetrahydro-4-quinazolinone
1-[1-Methyl-2-(1-piperazinyl)-ethyl]-2-phenyl-1,2,3,4-tetrahydro-4-quinazolinone
1-[1-Methyl-2-(1-methyl-4-piperazinyl)-ethyl]-2-phenyl-1,2,3,4-tetrahydro-4-quinazolinone
1-[1-Methyl-2-(1-benzyl-4-piperazinyl)-ethyl]-2-phenyl-1,2,3,4-tetrahydro-4-quinazolinone
1-[1-Methyl-2-(1-phenethyl-4-piperazinyl)-ethyl]-2-phenyl-1,2,3,4-tetrahydro-4-quinazolinone
1-[1-Methyl-2-(1-[p-aminophenethyl]-4-piperazinyl)-ethyl]-2-phenyl-1,2,3,4-tetrahydro-4-quinazolinone
6-Amino-1-[1-methyl-2-piperazinyl)-ethyl]-2-phenyl-1,2,3,4-tetrahydro-4-quinazolinone
6-Amino-1-[1-methyl-2-(1-methyl-4-piperazinyl)-ethyl]-2-phenyl-1,2,3,4-tetrahydro-4-quinazolinone
6-Amino-1-[1-methyl-2-(1-benzyl-4-piperazinyl)-ethyl]-2-phenyl-1,2,3,4-tetrahydro-4-quinazolinone
6-Amino-1-[1-methyl-2-(1-phenethyl-4-piperazinyl)-ethyl]-2-phenyl-1,2,3,4-tetrahydro-4-quinazolinone
6-Amino-1-[1-methyl-2-(1-[p-aminophenethyl]-4-piperazinyl)-ethyl]-2-phenyl-1,2,3,4-tetrahydro-4-quinazolinone Typical examples of analgesic intermediates of this invention are as follows:

2-[2-(4-[1-Phenyl]-piperazinyl)-ethylamino]-benzamide
3-Amino-2-[2-(1-phenyl-4-piperazinyl)-ethylamino]-benzamide
4-Amino-2-[2-(1-phenyl-4-piperazinyl)-ethylamino]-benzamide
5-Amino-2-[2-(1-phenyl-4-piperazinyl)-ethylamino]-benzamide
6-Amino-2-[2-(1-phenyl-4-piperazinyl)-ethylamino]-benzamide
3-Methoxy-2-[2-(1-phenyl-4-piperazinyl)-ethylamino]-benzamide
4-Methoxy-2-[2-(1-phenyl-4-piperazinyl)-ethylamino]-benzamide
5-Methoxy-2-[2-(1-phenyl-4-piperazinyl)-ethylamino]-benzamide
6-Methoxy-2-[2-(1-phenyl-4-piperazinyl)-ethylamino]-benzamide
3-Hydroxy-2-[2-(1-phenyl-4-piperazinyl)-ethylamino]-benzamide
4-Hydroxy-2-[2-(1-phenyl-4-piperazinyl)-ethylamino]-benzamide
5-Hydroxy-2-[2-(1-phenyl-4-piperazinyl)-ethylamino]-benzamide
6-Hydroxy-2-[2-(1-phenyl-4-piperazinyl)-ethylamino]-benzamide
3-Chloro-2-[2-(1-phenyl-4-piperazinyl)-ethylamino]-benzamide
4-Chloro-2-[2-(1-phenyl-4-piperazinyl)-ethylamino]-benzamide
5-Chloro-2-[2-(1-phenyl-4-piperazinyl)-ethylamino]-benzamide
6-Chloro-2-[2-(1-phenyl-4-piperazinyl)-ethylamino]-benzamide
3-Methyl-2-[2-(1-phenyl-4-piperazinyl)-ethylamino]-benzamide
4-Methyl-2-[2-(1-phenyl-4-piperazinyl)-ethylamino]-benzamide
5-Methyl-2-[2-(1-phenyl-4-piperazinyl)-ethylamino]-benzamide
6-Methyl-2-[2-(1-phenyl-4-piperazinyl)-ethylamino]-benzamide
3-Formamido-2-[2-(1-phenyl-4-piperazinyl)-ethylamino]-benzamide
4-Formamido-2-[2-(1-phenyl-4-piperazinyl)-ethylamino]-benzamide
5-Formamido-2-[2-(1-phenyl-4-piperazinyl)-ethylamino]-benzamide
6-Formamido-2-[2-(1-phenyl-4-piperazinyl)-ethylamino]-benzamide
2-[2-(1-Phenyl-4-piperazinyl)-ethylamino]-3-trifluoromethyl-benzamide
2-[2-(1-Phenyl-4-piperazinyl)-ethylamino]-4-trifluoromethyl-benzamide
2-[3-(1-Phenyl-4-piperazinyl)-propylamino]-benzamide
2-[1-Methyl-2-(1-phenyl-4-piperazinyl)-ethylamino]-benzamide
d-2-[1-Methyl-2-(1-phenyl-4-piperazinyl)-ethylamino]-benzamide
l-2-[1-Methyl-2-(1-phenyl-4-piperazinyl)-ethylamino]-benzamide
2-[2-Methyl-2-(1-phenyl-4-piperazinyl)-ethylamino]-benzamide
d-2-[2-Methyl-2-(1-phenyl-4-piperazinyl)-ethylamino]-benzamide
l-2-[2-Methyl-2-(1-phenyl-4-piperazinyl)-ethylamino]-benzamide
2-[2-(1-[o-Chlorophenyl]-4-piperazinyl)-ethylamino]-benzamide 2-[2-(1-[m-Chlorophenyl]-4-piperazinyl)-ethylamino]-benzamide
2-[2-(1-[p-Chlorophenyl]-4-piperazinyl)-ethylamino]-benzamide
2-[2-(1-[o-Aminophenyl]-4-piperazinyl)-ethylamino]-benzamide
2-[2-(1-[m-Aminophenyl]-4-piperazinyl)-ethylamino]-benzamide
2-[2-(1-[p-Aminophenyl]-4-piperazinyl)-ethylamino]-benzamide
2-[2-(1-[o-Methoxyphenyl]-4-piperazinyl)-ethylamino]-benzamide
2-[2-(1-[m-Methoxyphenyl]-4-piperazinyl)-ethylamino]-benzamide
2-[2-(1-[p-Methoxyphenyl]-4-piperazinyl)-ethylamino]-benzamide
2-[2-(1-[o-Hydroxyphenyl]-4-piperazinyl)-ethylamino]-benzamide
2-[2-(1-[m-Hydroxyphenyl]-4-piperazinyl)-ethylamino]-benzamide
2-[2-(1-[p-Hydroxyphenyl]-4-piperazinyl)-ethylamino]-benzamide
2-[2-(1-[o-Tolyl]-4-piperazinyl)-ethylamino]-benzamide
2-[2-(1-[m-Tolyl]-4-piperazinyl)-ethylamino]-benzamide
2-[2-(1-[p-Tolyl]-4-piperazinyl)-ethylamino]-benzamide
2-[3-(1-[o-Chlorophenyl]-4-piperazinyl)-propylamino]-benzamide
2-[3-(1-[m-Chlorophenyl]-4-piperazinyl)-propylamino]-benzamide
2-[3-(1-[p-Chlorophenyl]-4-piperazinyl)-propylamino]-benzamide
2-[3-(1-[o-Aminophenyl]-4-piperazinyl)-propylamino]-benzamide
2-[3-(1-[m-Aminophenyl]-4-piperazinyl)-propylamino]-benzamide
2-[3-(1-[p-Aminophenyl]-4-piperazinyl)-propylamino]-benzamide
2-[3-(1-[o-Methoxyphenyl]-4-piperazinyl)-propylamino]-benzamide
2-[3-(1-[m-Methoxyphenyl]-4-piperazinyl)-propylamino]-benzamide
2-[3-(1-p-Methoxyphenyl]-4-piperazinyl)-propylamino]-benzamide
2-[3-(1-[o-Hydroxyphenyl]-4-piperazinyl)-propylamino]-benzamide
2-[3-(1-[m-Hydroxyphenyl]-4-piperazinyl)-propylamino]-benzamide
2-[3-(1-[p-Hydroxyphenyl]-4-piperazinyl)-propylamino]-benzamide
2-[3-(1-[o-Tolyl]-4-piperazinyl)-propylamino]-benzamide
2-[3-(1-[m-Tolyl]-4-piperazinyl)-propylamino]-benzamide
2-[3-(1-[p-Tolyl]-4-piperazinyl)-propylamino]-benzamide
2-[1-Methyl-2-(1-[o-chlorophenyl]-4-piperazinyl)-ethylamino]-benzamide
d-2-[1-Methyl-2-(1-[o-chlorophenyl]-4-piperazinyl)-ethylamino]-benzamide
1-2-[1-Methyl-2-(1-[o-chlorophenyl]-4-piperazinyl)-ethylamino]-benzamide
2-[1-Methyl-2-(1-[m-chlorophenyl]-4-piperazinyl)-ethylamino]-benzamide
d-2-[1-Methyl-2-(1-[m-chlorophenyl]-4-piperazinyl)-ethylamino]-benzamide
1-2-[1-Methyl-2-(1-[m-chlorophenyl]-4-piperazinyl)-ethylamino]-benzamide
2-[1-Methyl-2-(1-[p-chlorophenyl]-4-piperazinyl)-ethylamino]-benzamide
d-2-[1-Methyl-2-(1-[p-chlorophenyl]-4-piperazinyl)-ethylamino]-benzamide
1-2-[1-Methyl-2-(1-[p-chlorophenyl]-4-piperazinyl)-ethylamino]-benzamide
2-[1-Methyl-2-(1-[o-Aminophenyl]-4-piperazinyl)-ethylamino]-benzamide
d-2-[1-Methyl-2-(1-[o-Aminophenyl]-4-piperazinyl)-ethylamino]-benzamide
1-2-[1-Methyl-2-(1-[o-Aminophenyl]-4-piperazinyl)-ethylamino]-benzamide
2-[1-Methyl-2-(1-[m-Aminophenyl]-4-piperazinyl)-ethylamino]-benzamide
d-2-[1-Methyl-2-(1-[m-Aminophenyl]-4-piperazinyl)-ethylamino]-benzamide
1-2-[1-Methyl-2-(1-[m-Aminophenyl]-4-piperazinyl)-ethylamino]-benzamide
2-[1-Methyl-2-(1-[p-Aminophenyl]-4-piperazinyl)-ethylamino]-benzamide
d-2-[1-Methyl-2-(1-[p-Aminophenyl]-4-piperazinyl)-ethylamino]-benzamide
1-2-[1-Methyl-2-(1-[p-Aminophenyl]-4-piperazinyl)-ethylamino]-benzamide
2-[1-Methyl-2-(1-[o-methoxyphenyl]-4-piperazinyl)-ethylamino]-benzamide
d-2-[1-Methyl-2-(1-[o-methoxyphenyl]-4-piperazinyl)-ethylamino]-benzamide
1-2-[1-Methyl-2-(1-[o-methoxyphenyl]-4-piperazinyl)-ethylamino]-benzamide
2-[1-Methyl-2-(1-[m-methoxyphenyl]-4-piperazinyl)-ethylamino]-benzamide
d-2-[1-Methyl-2-(1-[m-methoxyphenyl]-4-piperazinyl)-ethylamino]-benzamide
1-2-[1-Methyl-2-(1-[m-methoxyphenyl]-4-piperazinyl)-ethylamino]-benzamide
2-[1-Methyl-2-(1-[p-methoxyphenyl]-4-piperazinyl)-ethylamino]-benzamide
d-2-[1-Methyl-2-(1-[p-methoxyphenyl]-4-piperazinyl)-ethylamino]-benzamide
1-2-[1-Methyl-2-(1-[p-methoxyphenyl]-4-piperazinyl)-ethylamino]-benzamide
2-[1-Methyl-2-(1-[o-hydroxyphenyl]-4-piperazinyl)-ethylamino]-benzamide
d-2-[1-Methyl-2-(1-[o-hydroxyphenyl]-4-piperazinyl)-ethylamino]-benzamide
1-2-[1-Methyl-2-(1-[o-hydroxyphenyl]-4-piperazinyl)-ethylamino]-benzamide
2-[1-Methyl-2-(1-[m-hydroxyphenyl]-4-piperazinyl)-ethylamino]-benzamide
d-2-[1-Methyl-2-(1-[m-hydroxyphenyl]-4-piperazinyl)-ethylamino]-benzamide
1-2-[1-Methyl-2-(1-[m-hydroxyphenyl]-4-piperazinyl)-ethylamino]-benzamide
2-[1-Methyl-2-(1-[p-hydroxyphenyl]-4-piperazinyl)-ethylamino]-benzamide
d-2-[1-Methyl-2-(1-[p-hydroxyphenyl]-4-piperazinyl)-ethylamino]-benzamide
1-2-[1-Methyl-2-(1-[p-hydroxyphenyl]-4-piperazinyl)-ethylaminol]-benzamide
2-[1-Methyl-2-(1-[o-tolyl]-4-piperazinyl)-ethylamino]-benzamide
d-2-[1-Methyl-2-(1-[o-tolyl]-4-piperazinyl)-ethylamino]-benzamide
1-2-[1-Methyl-2-(1-[o-tolyl]-4-piperazinyl)-ethylamino]-benzamide 2-[1-Methyl-2-(1[m-tolyl]-4-piperazinyl)-ethylamino]-benzamide
d-2-[1-Methyl-2-(1-[m-tolyl]-4-piperazinyl)-ethylamino]-benzamide
1-2-[1-Methyl-2-(1-[m-tolyl]-4-piperazinyl)-ethylamino]-benzamide
2-[1-Methyl-2-(1-[p-tolyl]-4-piperazinyl)-ethylamino]-benzamide
d-2-[1-Methyl-2-(1-[p-tolyl]-4-piperazinyl)-ethylamino]-benzamide
1-2-[1-Methyl-2-(1-[p-tolyl]-4-piperazinyl)-ethylamino]-benzamide
2-[2-Methyl-2-(1-[o-chlorophenyl]-4-piperazinyl)-ethylamino]-benzamide
d-2-[2-Methyl-2-(1[o-chlorophenyl]-4-piperazinyl)-ethylamino]-benzamide
1-2-[2-Methyl-2-(1-[o-chlorophenyl]-4-piperazinyl)-ethylamino]-benzamide
2-[2-Methyl-2-(1-[m-chlorophenyl]-4-piperazinyl)-ethylamino]-benzamide
d-2-[2-Methyl-2-(1-[m-chlorophenyl]-4-piperazinyl)-ethylamino]-benzamide
1-2-[2-Methyl-2-(1-[m-chlorophenyl]-4-piperazinyl)-ethylamino]-benzamide
2-[2-Methyl-2-(1-[p-chlorophenyl]-4-piperazinyl)-ethylamino]-benzamide
d-2-[2-Methyl-2-(1[p-chlorophenyl]-4-piperazinyl)-ethylamino]-benzamide
1-2-[2-Methyl-2-(1-[p-chlorophenyl]-4-piperazinyl)-ethylamino]-benzamide
2-[2-Methyl-2-(1-[o-aminophenyl]-4-piperazinyl)-ethylamino]-benzamide
d-2-[2-Methyl-2-(1-[o-aminophenyl]-4-piperazinyl)-ethylamino]-benzamide
1-2-[2-Methyl-2-(1-[o-aminophenyl]-4-piperazinyl)-ethylamino]-benzamide
2-[2-Methyl-2-(1-[m-aminophenyl]-4-piperazinyl)-ethylamino]-benzamide
d-2-[2-Methyl-2-(1-[m-aminophenyl]-4-piperazinyl)-ethylamino]-benzamide
1-2-[2-Methyl-2-(1-[m-aminophenyl]-4-piperazinyl)-ethylamino]-benzamide
2-[2-Methyl-2-(1-[p-aminophenyl]-4-piperazinyl)-ethylamino]-benzamide
d-2-[2-Methyl-2-(1-[p-aminophenyl]-4-piperazinyl)-ethylamino]-benzamide
1-2-[2-Methyl-2-(1-[p-aminophenyl]-4-piperazinyl)-ethylamino]-benzamide
2-[2-Methyl-2-(1-[o-methoxyphenyl]-4-piperazinyl)-ethylamino]-benzamide
d-2-[2-Methyl-2-(1-[o-methoxyphenyl]-4-piperazinyl)-ethylamino]-benzamide
1-2-[2-Methyl-2-(1-[o-methoxyphenyl]-4-piperazinyl)-ethylamino]-benzamide
2-[2-Methyl-2-(1-[m-methoxyphenyl]-4-piperazinyl)-ethylamino]-benzamide
d-2-[2-Methyl-2-(1-[m-methoxyphenyl]-4-piperazinyl)-ethylamino]-benzamide
1-2-[2-Methyl-2-(1-[m-methoxyphenyl]-4-piperazinyl)-ethylamino]-benzamide
2-[2-Methyl-2-(1-[p-methoxyphenyl]-4-piperazinyl)-ethylamino]-benzamide
d-2-[2-Methyl-2-(1-[p-methoxyphenyl]-4-piperazinyl)-ethylamino]-benzamide
1-2-[2-Methyl-2-(1-[p-methoxyphenyl]-4-piperazinyl)-ethylamino]-benzamide
2-[2-Methyl-2-(1-[o-hydroxyphenyl]-4-piperazinyl)-ethylamino]-benzamide
d-2-[2-Methyl-2-(1-[o-hydroxylphenyl]-4-piperazinyl)-ethylamino]-benzamide
1-2-[2-Methyl-2-(1-[o-hydroxyphenyl]-4-piperazinyl)-ethylamino]-benzamide
2-[2-Methyl-2-(1-[m-hydroxyphenyl]-4-piperazinyl)-ethylamino]-benzamide
d-2-[2-Methyl-2-(1-[m-hydroxyphenyl]-4-piperazinyl)-ethylamino]-benzamide
1-2-[2-Methyl-2-(1-[m-hydroxyphenyl]-4-piperazinyl)-ethylamino]-benzamide
2-[2-Methyl-2-(1-[p-hydroxyphenyl]-4-piperazinyl)-ethylamino]-benzamide
d-2-[2-Methyl-2-(1-[p-hydroxyphenyl]-4-piperazinyl)-ethylamino]-benzamide
1-2-[2-Methyl-2-(1-[p-hydroxyphenyl]-4-piperazinyl)-ethylamino]-benzamide
2-[2-Methyl-2-(1-[o-tolyl]-4-piperazinyl)-ethylamino]-benzamide
d-2-[2-Methyl-2-(1-[o-tolyl]-4-piperazinyl)-ethylamino]-benzamide
1-2-[2-Methyl-2-(1-[o-tolyl]-4-piperazinyl)-ethylamino]-benzamide
2-[2-Methyl-2-(1-[m-tolyl]-4-piperazinyl)-ethylamino]-benzamide
d-2-[2-Methyl-2-(1-[m-tolyl]-4-piperazinyl)-ethylamino]-benzamide
1-2-[2-Methyl-2-(1-[m-tolyl]-4-piperazinyl)-ethylamino]-benzamide
2-[2-Methyl-2-(1-[p-tolyl]-4-piperazinyl)-ethylamino]-benzamide
d-2-[2-Methyl-2-(1-[p-tolyl]-4-piperazinyl)-ethylamino]-benzarnide
1-2-[2-Methyl-2-(1-[p-toly]-4-piperazinyl)-ethylamino]-benzamide
2-[2-(2-Methyl-1-phenyl-4-piperazinyl)-ethylamino]-benzamide
N-Methyl-2-[2-(1-phenyl-4-piperazinyl)-ethylamino]-benzamide
2-[2-(1-Methyl-4-piperazinyl)-ethylamino]-benzamide
2-[2-(2-Benzyl-4-piperazinyl)-ethylamino]-benzamide
2-[2-(1-Phenethyl-4-piperazinyl)-ethylamino]-benzamide
2-[2-(1-[p-Aminophenethyl]-4-piperazinyl)-ethylamino]-benzamide
2-[1-Methyl-2-(1-methyl-4-piperazinyl)-ethylamino]-benzamide
2-[1-Methyl-2-(1-benzyl-4-piperazinyl)-ethylamino]-benzamide
2-[1-Methyl-2-(1-phenethyl-4-piperazinyl)-ethylamino]-benzamide
2-[1-Methyl-2-(1-[p-aminophenethyl]-4-piperazinyl)-ethylamino]-benzamide
5-Amino-2-[1-methyl-2-(1-piperazinyl)-ethylamino]-benzamide
5-Amino-2-[1-methyl-2-(1-methyl-4-piperazinyl)-ethylamino]-benzamide
5-Amino-2-[1-methyl-2-(1-benzyl-4-piperazinyl)-ethylamino]-benzamide
5-Amino-2-[1-methyl-2-(1-phenethyl-4-piperazinyl)-ethylamino]-benzamide
5-Amino-2-[1-methyl-2-(1-[p-aminophenethyl]-4-piperazinyl)-ethylamino]-benzamide.
5-Amino-2-[1-methyl-2-(1-phenyl-4-piperazinyl)-ethylamino]-benzamide
2-[N-Benzoyl-2-(1-phenyl-4-piperazinyl)-ethylamino]-benzamide 2-[N-(o-Chlorobenzoyl)-2-(1-phenyl-4-piperazinyl)-ethylamino]-benzamide
2-[N-(m-Chlorobenzoyl)-2-(1-phenyl-4-piperazinyl)-ethylamino]-benzamide
2-[N-(p-Chlorobenzoyl)-2-(1-phenyl-4-piperazinyl)-ethylamino]-benzamide
2-[N-(o-Aminobenzoyl)-2-(1-phenyl-4-piperazinyl)-ethylamino]-benzamide
2-[N-(m-Aminobenzoyl)-2-(1-phenyl-4-piperazinyl)-ethylamino]-benzamide
2-[N-(p-Aminobenzoyl)-2-(1-phenyl-4-piperazinyl)-ethylamino]-benzamide
2-[N-(o-Methoxybenzoyl)-2-(1-phenyl-4-piperazinyl)-ethylamino]-benzamide
2-[N-(m-Methoxybenzoyl)-2-(1-phenyl-4-piperazinyl)-ethylamino]-benzamide
2-[N-(p-Methoxybenzoyl)-2-(1-phenyl-4-piperazinyl)-ethylamino]-benzamide
2-[N-(o-Hydroxybenzoyl)-2-[1-phenyl-4-Piperazinyl)-ethylamino]-benzamide
2-[N-(m-Hydroxybenzoyl)-2-(1-phenyl-4-piperazinyl)-ethylamino]-benzamide
2-[N-(p-Hydroxybenzoyl)-2-(1-phenyl-4-piperazinyl)-ethylamino]-benzamide
2-[N-(o-Methylbenzoyl)-2-(1-phenyl-4-piperazinyl)-ethylamino]-benzamide
2-[N-(m-Methylbenzoyl)-2-(1-phenyl-4-piperazinyl)-ethylamino]-benzamide
2-[N-(p-Methylbenzoyl)-2-(1-phenyl-4-piperazinyl)-ethylamino]-benzamide
2-[N-Benzyl-2-(1-phenyl-4-piperazinyl)-ethylamino]-benzamide
2-[N-Benzyl-1-methyl-2-(1-phenyl-4-piperazinyl)-ethylamino]-benzamide
2-[N-(o-Chlorobenzyl)-2-(1-phenyl-4-piperazinyl)-ethylamino]-benzamide
2-[N-(m-Chlorobenzyl)-2-(1-phenyl-4-piperazinyl)-ethylamino]-benzamide
2-[N-(p-Chlorobenzyl)-2-(1-phenyl-4-piperazinyl)-ethylamino]-benzamide
2-[N-(o-Aminobenzyl)-2-(1-phenyl-4-piperazinyl)-ethylamino]-benzamide
2-[N-(m-Aminobenzyl)-2-(1-phenyl-4-piperazinyl)-ethylamino]-benzamide
2-[N-(p-Aminobenzyl)-2-(1-phenyl-4-piperazinyl)-ethylamino]-benzamide
2-[N-(o-Methylbenzyl)-2-(1-phenyl-4-piperazinyl)-ethylamino]-benzamide
2-[N-(m-Methylbenzyl)-2-(1-phenyl-4-piperazinyl)-ethylamino]-benzamide
2-[N-(p-Methylbenzyl)-2-(1-phenyl-4-piperazinyl)-ethylamino]-benzamide
2-[N-(o-Methoxybenzyl)-2-(1-phenyl-4-piperazinyl)-ethylamino]-benzamide
2-[N-(m-Methoxybenzyl)-2-(1-phenyl-4-piperazinyl)-ethylamino]-benzamide
2-[N-(p-Methoxybenzyl)-2-(1-phenyl-4-piperazinyl)-ethylamino]-benzamide
2-[N-(o-Hydroxybenzyl)-2-(1-phenyl-4-piperazinyl)-ethylamino]-benzamide
2-[N-(m-Hydroxybenzyl)-2-(1-phenyl-4-piperazinyl)-ethylamino]-benzamide
2-[N-(p-Hydroxybenzyl)-2-(1-phenyl-4-piperazinyl)-ethylamino]-benzamide
2-[N-Picolinoyl-2-(1-phenyl-4-piperazinyl)-ethylamino]-benzamide
2-[N-Nicotinoyl-2-(1-phenyl-4-piperazinyl)-ethylamino]-benzamide
2-[N-Isonicotinoyl-2-(1-phenyl-4-piperazinyl)-ethylamino]-benzamide
2-[N-(2-Pyridylmethyl)-2-(1-phenyl-4-piperazinyl)-ethylamino]benzamide
2-[N-(3-Pyridylmethyl)-2-(1-phenyl-4-piperazinyl)-ethylamino]-benzamide
2-[N-(4-Pyridylmethyl)-2-(1-phenyl-4-piperazinyl)-ethylamino]-benzamide
2-[N-Acetyl-2-(1-phenyl-4-piperazinyl)-ethylamino]-benzamide
2-[N-Propionyl-2-(1-phenyl-4-piperazinyl)-ethylamino]-benzamide
2-[N-Butyryl-2-(1-phenyl-4-piperazinyl)-ethylamino]-benzamide
2-[N-Acetyl-1-methyl-2-(1-phenyl-4-piperazinyl)-ethylamino]-benzamide
2-[N-Propionyl-1-methyl-2-(1-phenyl-4-piperazinyl)-ethylamino]-benzamide
2-[N-Methyl-2-(1-phenyl-4-piperazinyl)-ethylamino]-benzamide
2-[N-Ethyl-2-(1-phenyl-4-piperazinyl)-ethylamino]-benzamide
2-[N-Propyl-2-(1-phenyl-4-piperazinyl)-ethylamino]-benzamide
2-[N-Butyl-2-(1-phenyl-4-piperazinyl)-ethylamino]-benzamide
3-Chloro-2-[3-(1-phenyl-4-piperazinyl)-propylamino]-benzamide
4-Chloro-2-[3-(1-phenyl-4-piperazinyl)-propylamino]-benzamide
5-Chloro-2-[3-(1-phenyl-4-piperazinyl)-propylamino]-benzamide
6-Chloro-2-[3-(1-phenyl-4-piperazinyl)-propylamino]-benzamide
3-Amino-2-[3-(1-phenyl-4-piperazinyl)-propylamino]-benzamide
4-Amino-2-[3-(1-phenyl-4-piperazinyl)-propylamino]-benzamide
5-Amino-2-[3-(1-phenyl-4-piperazinyl)-propylamino]-benzamide
6-Amino-2-[3-(1-phenyl-4-piperazinyl)-propylamino]-benzamide
3-Methoxy-2-[3-(1-phenyl-4-piperazinyl)-propylamino]-benzamide
4-Methoxy-2-[3-(1-phenyl-4-piperazinyl)-propylamino]-benzamide
5-Methoxy-2-[3-(1-phenyl-4-piperazinyl)-propylamino]-benzamide
6-Methoxy-2-[3-(1-phenyl-4-piperazinyl)-propylamino]-benzamide
3-Hydroxy-2-[3-(1-phenyl-4-piperazinyl)-propylamino]-benzamide
4-Hydroxy-2-[3-(1-phenyl-4-piperazinyl)-propylamino]-benzamide
5-Hydroxy-2-[3-(1-phenyl-4-piperazinyl)-propylamino]-benzamide
6-Hydroxy-2-[3-(1-phenyl-4-piperazinyl)-propylamino]-benzamide
3-Methyl-2-[3-(1-phenyl-4-piperazinyl)-propylamino]-benzamide
4-Methyl-2-[3-(1-phenyl-4-piperazinyl)-propylamino]-benzamide
5-Methyl-2-[3-(1-phenyl-4-piperazinyl)-propylamino]-benzamide
6-Methyl-2-[3-(1-phenyl-piperazinyl)-propylamino]-benzamide
2-[3-(1-phenyl-4-piperazinyl)-propylamino]-3-trifluoromethylbenzamide 2-[3-(1-phenyl-4-piperazinyl)-propylamino]-4-trifluoromethylbenzamide
2-[3-(1-phenyl-4-piperazinyl)-propylamino]-5-trifluoromethylbenzamide
2-[3-(1-phenyl-4-piperazinyl)-propylamino]-6-trifluoromethylbenzamide
3-Chloro-2-[1-methyl-2-(1-phenyl-4-piperazinyl)-ethylamino]-benzamide
4-Chloro-2-[1-methyl-2-(1-phenyl-4-piperazinyl)-ethylamino]-benzamide
5-Chloro-2-[1-methyl-2-(1-phenyl-4-piperazinyl)-ethylamino]-benzamide
6-Chloro-2-[1-methyl-2-(1-phenyl-4-piperazinyl)-ethylamino]-benzamide
3-Amino-2-[1-methyl-2-(1-phenyl-4-piperazinyl)-ethylamino]-benzamide
4-Amino-2-[1-methyl-2-(1-phenyl-4-piperazinyl)-ethylamino]-benzamide
5-Amino-2-[1-methyl-2-(1-phenyl-4-piperazinyl)-ethylamino]-benzamide
6-Amino-2-[1-methyl-2-(1-phenyl-4-piperazinyl)-ethylamino]-benzamide
3-Methoxy-2-[1-methyl-2-(1-phenyl-4-piperazinyl)-ethylamino]-benzamide
4-Methoxy-2-[1-methyl-2-(1-phenyl-4-piperazinyl)-ethylamino]-benzamide
5-Methoxy-2-[1-methyl-2-(1-phenyl-4-piperazinyl)-ethylamino]-benzamide
6-Methoxy-2-[1-methyl-2-(1-phenyl-4-piperazinyl)-ethylamino]-benzamide
3-Hydroxy-2-[1-methyl-2-(1-phenyl-4-piperazinyl)-ethylamino]-benzamide
4-Hydroxy-2-[1-methyl-2-(1-phenyl-4-piperazinyl)-ethylamino]-benzamide
5-Hydroxy-2-[1-methyl-2-(1-phenyl-4-piperazinyl)-ethylamino]-benzamide
6-Hydroxy-2-[1-methyl-2-(1-phenyl-4-piperazinyl)-ethylamino]-benzamide
3-Methyl-2-[1-methyl-2-(1-phenyl-4-piperazinyl)-ethylamino]-benzamide
4-Methyl-2-[1-methyl-2-(1-phenyl-4-piperazinyl)-ethylamino]-benzamide
5-Methyl-2-[1-methyl-2-(1-phenyl-4-piperazinyl)-ethylamino]-benzamide
6-Methyl-2-[1-methyl-2-(1-phenyl-4-piperazinyl)-ethylamino]-benzamide
2-[1-Methyl-2-(1-phenyl-4-piperazinyl)-ethylamino]-3-trifluoromethylbenzamide
2-[1-Methyl-2-(1-phenyl-4-piperazinyl)-ethylamino]-4-trifluoromethylbenzamide
2-[1-Methyl-2-(1-phenyl-4-piperazinyl)-ethylamino]-5-trifluoromethylbenzamide
2-[1-Methyl-2-(1-phenyl-4-piperazinyl)-ethylamino]-6-trifluoromethylbenzamide
3-Chloro-2-[2-methyl-2-(1-phenyl-4-piperazinyl)-ethylamino]-benzamide
4-Chloro-2-[2-methyl-2-(1-phenyl-4-piperazinyl)-ethylamino]-benzamide
5-Chloro-2-[2-methyl-2-(1-phenyl-4-piperazinyl)-ethylamino]-benzamide
6-Chloro-2-[2-methyl-2-(1-phenyl-4-piperazinyl)-ethylamino]-benzamide
3-Amino-2-[2-methyl-2-(1-phenyl-4-piperazinyl)-ethylamino]-benzamide
4-Amino-2-[2-methyl-2-(1-phenyl-4-piperazinyl)-ethylamino]-benzamide
5-Amino-2-[2-methyl-2-(1-phenyl-4-piperazinyl)-ethylamino]-benzamide
6-Amino-2-[2-methyl-2-(1-phenyl-4-piperazinyl)-ethylamino]-benzamide
3-Methoxy-2-[2-methyl-2-(1-phenyl-4-piperazinyl)-ethylamino]-benzamide
4-Methoxy-2-[2-methyl-2-(1-phenyl-4-piperazinyl)-ethylamino]-benzamide
5-Methoxy-2-[2-methyl-2-(1-phenyl-4-piperazinyl)-ethylamino]-benzamide
6-Methoxy-2-[2-methyl-2-(1-phenyl-4-piperazinyl)-ethylamino]-benzamide
3-Hydroxy-2-[2-methyl-2-(1-phenyl-4-piperazinyl)-ethylamino]-benzamide
4-Hydroxy-2-[2-methyl-2-(1-phenyl-4-piperazinyl)-ethylamino]-benzamide
5-Hydroxy-2-[2-methyl-2-(1-phenyl-4-piperazinyl)-ethylamino]-benzamide
6-Hydroxy-2-[2-methyl-2-(1-phenyl-4-piperazinyl)-ethylamino]-benzamide
3-Methyl-2-[2-methyl-2-(1-phenyl-4-piperazinyl)-ethylamino]-benzamide
4-Methyl-2-[2-methyl-2-(1-phenyl-4-piperazinyl)-ethylamino]-benzamide
5-Methyl-2-[2-methyl-2-(1-phenyl-4-piperazinyl)-ethylamino]-benzamide
6-Methyl-2-[2-methyl-2-(1-phenyl-4-piperazinyl)-ethylamino]-benzamide
2-[2-Methyl-2-(1-phenyl-4-piperazinyl)-ethylamino]-3-trifluoromethylbenzamide
2-[2-Methyl-2-(1-phenyl-4-piperazinyl)-ethylamino]-4-trifluoromethylbenzamide
2-[2-Methyl-2-(1-phenyl-4-piperazinyl)-ethylamino]-5-trifluoromethylbenzamide
2-[2-Methyl-2-(1-phenyl-4-piperazinyl)-ethylamino]-6-trifluoromethylbenzamide
1-(2-[2-(1-phenyl-4-piperazinyl)-ethylamino]-benzoyl)-piperidine
1-(3-Amino-2-[2-(1-phenyl-4-piperazinyl)-ethylamino]-benzoyl)-piperidine
1-(4-Amino-2-[2-(1-phenyl-4-piperazinyl)-ethylamino]-benzoyl)-piperidine
1-(5-Amino-2-[2-(1-phenyl-4-piperazinyl)-ethylamino]-benzoyl)-piperidine
1-(6-Amino-2-[2-(1-phenyl-4-piperazinyl)-ethylamino]-benzoyl)-piperidine
1-(3-Methoxy-2-[2-(1-phenyl-4-piperazinyl)-ethylamino]-benzoyl)-piperidine
1-(4-Methoxy-2-[2-(1-phenyl-4-piperazinyl)-ethylamino]-benzoyl)-piperidine
1-(5-Methoxy-2-[2-(1-phenyl-4-piperazinyl)-ethylamino]-benzoyl)-piperidine
1-(6-Methoxy-2-[2-(1-phenyl-4-piperazinyl)-ethylamino]-benzoyl)-piperidine
1-(3-Hydroxy-2-[2-(1-phenyl-4-piperazinyl)-ethylamino]-benzoyl)-piperidine
1-(4-Hydroxy-2-[2-(1-phenyl-4-piperazinyl)-ethylamino]-benzoyl)-piperidine
1-(5-Hydroxy-2-[2-(1-phenyl-4-piperazinyl)-ethylamino]-benzoyl)-piperidine
1-(6-Hydroxy-2-[2-(1-phenyl-4-piperazinyl)-ethylamino]-benzoyl)-piperidine
4-(2-[1-phenyl-4-piperazinyl)-ethylamino]-benzoyl)-morpholine
4-(3-Amino-2-[2-(1-phenyl-4-piperazinyl)-ethylamino]-benzoyl)-morpholine
4-(4-Amino-2-[2-(1-phenyl-4-piperazinyl)-ethylamino]-benzoyl)-morpholine
4-(5-Amino-2-[2-(1-phenyl-4-piperazinyl)-ethylamino]-benzoyl)-morpholine 4-(6-Amino-2-[2-(1-phenyl-4-piperazinyl)-ethylamino]-benzoyl)-morpholine
4-(3-Methoxy-2-[2-(1-phenyl-4-piperazinyl)-ethylamino]-benzoyl)-morpholine
4-(4-Methoxy-2-[2-(1-phenyl-4-piperazinyl)-ethylamino]-benzoyl)-morpholine
4-(5-Methoxy-2-[2-(1-phenyl-4-piperazinyl)-ethylamino]-benzoyl)-morpholine
4-(6-Methoxy-2-[2-(1-phenyl-4-piperazinyl)-ethylamino]-benzoyl)-morpholine
4-(3-Hydroxy-2-[2-(1-phenyl-4-piperazinyl)-ethylamino]-benzoyl)-morpholine
4-(4-Hydroxy-2-[2-(1-phenyl-4-piperazinyl)-ethylamino]-benzoyl)-morpholine
4-(5-Hydroxy-2-[2-(1-phenyl-4-piperazinyl)-ethylamino]-benzoyl)-morpholine
4-(6-Hydroxy-2-[2-(1-phenyl-4-piperazinyl)-ethylamino]-benzoyl)-morpholine
1-(2-[2-(1-Phenyl-4-piperazinyl)-ethylamino]-benzoyl)-pyrrolidine
1-(3-Amino-2-[2-(1-phenyl-4-piperazinyl)-ethylamino]-benzoyl)-pyrrolidine
1-(4-Amino-2-[2-(1-phenyl-4-piperazinyl)-ethylamino]-benzoyl)-pyrrolidine
1-(5-Amino-2-[2-(1-phenyl-4-piperazinyl)-ethylamino]-benzoyl)-pyrrolidine
1-(6-Amino-2-[2-(1-phenyl-4-piperazinyl)-ethylamino]-benzoyl)-pyrrolidine
1-(3-Hydroxy-2-[2-(1-phenyl-4-piperazinyl)-ethylamino]-benzoyl)-pyrrolidine
1-(4-Hydroxy-2-[2-(1-phenyl-4-piperazinyl)-ethylamino]-benzoyl)-pyrrolidine
1-(5-Hydroxy-2-[2-(1-phenyl-4-piperazinyl)-ethylamino]-benzoyl)-pyrrolidine
1-(6-Hydroxy-2-[2-(1-phenyl-4-piperazinyl)-ethylamino]-benzoyl)-pyrrolidine
1-(3-Methoxy-2-[2-(1-phenyl-4-piperazinyl)-ethylamino]-benzoyl)-pyrrolidine
1-(4-Methoxy-2-[2-(1-phenyl-4-piperazinyl)-ethylamino]-benzoyl)-pyrrolidine
1-(5-Methoxy-2-[2-(1-phenyl-4-piperazinyl)-ethylamino]-benzoyl)-pyrrolidine
1-(6-Methoxy-2-[2-(1-phenyl-4-piperazinyl)-ethylamino]-benzoyl)-pyrrolidine
3-Amino-N-methyl-2-[2-(1-phenyl-4-piperazinyl)-ethylamino]-benzamide
4-Amino-N-methyl-2-[2-(1-phenyl-4-piperazinyl)-ethylamino]-benzamide
5-Amino-N-methyl-2-[2-(1-phenyl-4-piperazinyl)-ethylamino]-benzamide
6-Amino-N-methyl-2-[2-(1-phenyl-4-piperazinyl)-ethylamino]-benzamide
3-Methoxy-N-methyl-2-[2-(1-phenyl-4-piperazinyl)-ethylamino]-benzamide
4-Methoxy-N-methyl-2-[2-(1-phenyl-4-piperazinyl)-ethylamino]-benzamide
5-Methoxy-N-methyl-2-[2-(1-phenyl-4-piperazinyl)-ethylamino]-benzamide
6-Methoxy-N-methyl-2-[2-(1-phenyl-4-piperazinyl)-ethylamino]-benzamide
3-Hydroxy-N-methyl-2-[2-(1-phenyl-4-piperazinyl)-ethylamino]-benzamide
4-Hydroxy-N-methyl-2-[2-(1-phenyl-4-piperazinyl)-ethylamino]-benzamide
5-Hydroxy-N-methyl-2-[2-(1-phenyl-4-piperazinyl)-ethylamino]-benzamide
6-Hydroxy-N-methyl-2-[2-(1-phenyl-4-piperazinyl)-ethylamino]-benzamide
N,N-Dimethyl-2-[2-(1-phenyl-4-piperazinyl)-ethylamino]-benzamide
3-Amino-N,N-dimethyl-2-[2-(1-phenyl-4-piperazinyl)-ethylamino]-benzamide
4-Amino-N,N-dimethyl-2-[2-(1-phenyl-4-piperazinyl)-ethylamino]-benzamide
5-Amino-N,N-dimethyl-2-[2-(1-phenyl-4-piperazinyl)-ethylamino]-benzamide
6-Amino-N,N-dimethyl-2-[2-(1-phenyl-4-piperazinyl)-ethylamino]-benzamide
3-Methoxy-N,N-dimethyl-2-[2-(1-phenyl-4-piperazinyl)-ethylamino]-benzamide
4-Methoxy-N,N-dimethyl-2-[2-(1-phenyl-4-piperazinyl)-ethylamino]-benzamide
5-Methoxy-N,N-dimethyl-2-[2-(1-phenyl-4-piperazinyl)-ethylamino]-benzamide
6-Methoxy-N,N-dimethyl-2-[2-(1-phenyl-4-piperazinyl)-ethylamino]-benzamide
3-Hydroxy-N,N-dimethyl-2-[2-(1-phenyl-4-piperazinyl)-ethylamino]-benzamide
4-Hydroxy-N,N-dimethyl-2-[2-(1-phenyl-4-piperazinyl)-ethylamino]-benzamide
5-Hydroxy-N,N-dimethyl-2-[2-(1-phenyl-4-piperazinyl)-ethylamino]-benzamide
6-Hydroxy-N,N-dimethyl-2-[2-(1-phenyl-4-piperazinyl)-ethylamino]-benzamide
2-[1-phenyl-4-piperazinylmethylamino]-benzamide
2-[2-1-α-Methylphenethyl-4-piperazinyl)-ethylamino]-benzamide
2-[2-(1-[o-Amino-α-methylphenethyl]-4-piperazinyl)-ethylamino]-benzamide
2-[2-(1-[m-Amino-α-methylphenethyl]-4-piperazinyl)-ethylamino]-benzamide
2-[2-(1-[p-Amino-α-methylphenethyl]-4-piperazinyl)-ethylamino]-benzamide
2-[2-(1-[o-Methoxy-α-methylphenethyl]-4-piperazinyl)-ethylamino]-benzamide
2-[2-(1-[m-Methoxy-α-methylphenethyl]-4-piperazinyl)-ethylamino]-benzamide
2-[2-(1-[p-Methoxy-α-methylphenethyl]-4-piperazinyl)-ethylamino]-benzamide
2-[2-(1-[o-Hydroxy-α-methylphenethyl]-4-piperazinyl)-ethylamino]-benzamide
2-[2-(1-[m-Hydroxy-α-methylphenethyl]-4-piperazinyl)-ethylamino]-benzamide
2-[2-(1-[p-Hydroxy-α-methylphenethyl]-4-piperazinyl)-ethylamino]-benzamide
2-[2-(1-phenyl-4-piperazinyl)-ethylamino]-benzoic acid
Methyl 2-[2-(1-phenyl4-piperazinyl)-ethylamino]-benzoate
3-Amino-2-[2-(1phenyl-4-piperazinyl)-ethylamino]-benzoic acid
4-Amino-2-[2-(1-phenyl-4-piperazinyl)-ethylamino]-benzoic acid
5-Amino-2-[2-(1-phenyl-4-piperazinyl)-ethylamino]-benzoic acid
6-Amino-2-[2-(1-phenyl-4-piperazinyl)-ethylamino]-benzoic acid
Methyl 3-Amino-2-[2-(1-phenyl-4-piperazinyl)-ethylamino]-benzoate
Methyl 4-Amino-2-[2-(1-phenyl-4-piperazinyl)-ethylamino]-benzoate
Methyl 5-Amino-2-[2-(1-phenyl-4-piperazinyl)-ethylamino]-benzoate
Methyl 6-Amino-2-[2-(1-phenyl-4-piperazinyl)-ethylamino]-benzoate 3-Methoxy-2-[2-(1-phenyl-4-piperazinyl)-ethylamino]-benzoic acid
4-Methoxy-2-[2-(1-phenyl-4-piperazinyl)-ethylamino]-benzoic acid
5-Methoxy-2-[2-(1-phenyl-4-piperazinyl)-ethylamino]-benzoic acid
6-Methoxy-2-[2-(1-phenyl-4-piperazinyl)-ethylamino]-benzoic acid
Methyl 3-Methoxy-2-[2-(1-phenyl-4-piperazinyl)-ethylamino]-benzoate
Methyl 4-Methoxy-2-[2-(1-phenyl-4-piperazinyl)-ethylamino]-benzoate
Methyl 5-Methoxy-2-[2-(1-phenyl-4-piperazinyl)-ethylamino]-benzoate
Methyl 6-Methoxy-2-[2-(1-phenyl-4-piperazinyl)-ethylamino]-benzoate
3-Hydroxy-2-[2-(1-phenyl-4piperazinyl)-ethylamino]-benzoic acid
4-Hydroxy-2-[2-(1-phenyl-4-piperazinyl)-ethylamino]-benzoic acid
5-Hydroxy-2-[2-(1-phenyl-4-piperazinyl)-ethylamino]-benzoic acid
6-Hydroxy-2-[2-(1-phenyl-4-piperazinyl)-ethylamino]-benzoic acid
Methyl 3-Hydroxy-2-[2-(1-phenyl-4piperazinyl)-ethylamino]-benzoate
Methyl 4-Hydroxy-2-[2-(1-phenyl-4-piperazinyl)-ethylamino]-benzoate
Methyl 5-Hydroxy-2-[2-1-phenyl-4-piperazinyl)-ethylamino]-benzoate
Methyl 6-Hydroxy-2-[2-(1-phenyl-4-piperazinyl)-ethylamino]-benzoate
Methyl 2-[1-Methyl-2-(1-phenyl-4-piperazinyl)-ethylamino]-benzoate
Methyl 3-Amino-2-[1-methyl-2-(1-phenyl-4-piperazinyl)-ethylamino]-benzoate
Methyl 4-Amino-2[1-methyl-2-(1-phenyl-4-piperazinyl)-ethylamino]-benzoate
Methyl 5-Amino-2-[1-methyl-2-(1-phenyl-4-piperazinyl)-ethylamino]-benzoate
Methyl 6-Amino-2-[1-methyl-2-(1-phenyl-4-piperazinyl)-ethylamino]-benzoate
Methyl 3-Methoxy-2-[1-methyl-2-(1-phenyl-4-piperazinyl)-ethylamino]-benzoate
Methyl 4-Methoxy-2-[1-methyl-2-(1-phenyl-4-piperazinyl)-ethylamino]-benzoate
Methyl 5-Methoxy-2-[1-methyl-2-(1-phenyl-4-piperazinyl)-ethylamino]-benzoate
Methyl 6-Methoxy-2-[1-methyl-2-(1-phenyl-4-piperazinyl)-ethylamino]-benzoate
Methyl 3-Hydroxy-2-(1-methyl-2-(1-phenyl-4-piperazinyl)-ethylamino]-benzoate
Methyl 4-Hydroxy-2-(1-methyl-2-(1-phenyl-4-piperazinyl)-ethylamino]-benzoate
Methyl 5-Hydroxy-2-(1-methyl-2-(1-phenyl-4-piperazinyl)-ethylamino]-benzoate
Methyl 6-Hydroxy-2-(1-methyl-2-(1-phenyl-4-piperazinyl)-ethylamino]-benzoate
Methyl 2-[N-Benzoyl-2-(1-phenyl-4-piperazinyl)-ethylamino]-benzoate
Methyl 3-Amino-2-[N-benzoyl-2-(1-phenyl-4-piperazinyl)-ethylamino]-benzoate
Methyl 4-Amino-2-[N-benzoyl-2-(1-phenyl-4-piperazinyl)-ethylamino]-benzoate
Methyl 5-Amino-2-[N-benzoyl-2-(1-phenyl-4-piperazinyl)-ethylamino]-benzoate
Methyl 6-Amino-2-[N-benzoyl-2-(1-phenyl-4-piperazinyl)-ethylamino]-benzoate
Methyl 3-Methoxy-2-[N-benzoyl-2-(1-phenyl-4-piperazinyl)-ethylamino]-benzoate
Methyl 4-Methoxy-2-[N-benzoyl-2-(1-phenyl-4-piperazinyl)-ethylamino]-benzoate
Methyl 5-Methoxy-2-[N-benzoyl-2-(1-phenyl-4-piperazinyl)-ethylamino]-benzoate
Methyl 6-Methoxy-2-[N-benzoyl-2-(1-phenyl-4-piperazinyl)-ethylamino]-benzoate
Methyl 3-Hydroxy-2-[N-benzoyl-2-(1-phenyl-4-piperazinyl)-ethylamino]-benzoate
Methyl 4-Hydroxy-2-[N-benzoyl-2-(1-phenyl-4-piperazinyl)-ethylamino]-benzoate
Methyl 5-Hydroxy-2-[N-benzoyl-2-(1-phenyl-4-piperazinyl)-ethylamino]-benzoate
Methyl 6-Hydroxy-2-[N-benzoyl-2-(1-phenyl-4-piperazinyl)-ethylamino]-benzoate
Methyl 2-[N-Benzyl-2-(1-phenyl-4-piperazinyl)-ethylamino]-benzoate
Methyl 3-Amino-2-[N-benzyl-2-(1-phenyl-4-piperazinyl)-ethylamino]-benzoate
Methyl 4-Amino-2-[N-benzyl-2-(1-phenyl-4-piperazinyl)-ethylamino]-benzoate
Methyl 5-Amino-2-[N-benzyl-2-(1-phenyl-4-piperazinyl)-ethylamino]-benzoate
Methyl 6-Amino-2-[N-benzyl-2-(1-phenyl-4-piperazinyl)-ethylamino]-benzoate
Methyl 3-Methoxy-2-[N-benzyl-2-(1-phenyl-4-piperazinyl)-ethylamino]-benzoate
Methyl 4-Methoxy-2-[N-benzyl-2-(1-phenyl-4-piperazinyl)-ethylamino]-benzoate
Methyl 5-Methoxy-2-[N-benzyl-2-(1-phenyl-4-piperazinyl)-ethylamino]-benzoate
Methyl 6-Methoxy-2-[N-benzyl-2-(1-phenyl-4-piperazinyl)-ethylamino]-benzoate
Methyl 3-Hydroxy-2-[N-benzyl-2-(1-phenyl-4-piperazinyl)-ethylamino]-benzoate
Methyl 4-Hydroxy-2-[N-benzyl-2-(1-phenyl-4-piperazinyl)-ethylamino]-benzoate
Methyl 5-Hydroxy-2-[N-benzyl-2-(1-phenyl-4-piperazinyl)-ethylamino]-benzoate
Methyl 6-Hydroxy-2-[N-benzyl-2-(1-phenyl-4-piperazinyl)-ethylamino]-benzoate
Methyl 2-[N-Picolinoyl-2-(1-phenyl-4-piperazinyl)-ethylamino]-benzoate
Methyl 3-Amino-2-[N-picolinoyl-2-(1-phenyl-4-piperazinyl)-ethylamino]-benzoate
Methyl 4-Amino-2-[N-picolinoyl-2-(1-phenyl-4-piperazinyl)-ethylamino]-benzoate
Methyl 5-Amino-2-[N-picolinoyl-2-(1-phenyl-4-piperazinyl)-ethylamino]-benzoate
Methyl 6-Amino-2-[N-picolinoyl-2-(1-phenyl-4-piperazinyl)-ethylamino]-benzoate
Methyl 3-Methoxy-2-[N-picolinoyl-2-(1-phenyl-4-piperazinyl)-ethylamino]-benzoate
Methyl 4-Methoxy-2-[N-picolinoyl-2-(1-phenyl-4-piperazinyl)-ethylamino]-benzoate
Methyl 5-Methoxy-2-[N-picolinoyl-2-(1-phenyl-4-piperazinyl)-ethylamino]-benzoate
Methyl 6-Methoxy-2-[N-picolinoyl-2-(1-phenyl-4-piperazinyl)-ethylamino]-benzoate
Methyl 3-Hydroxy-2-[N-picolinoyl-2-(1-phenyl-4-piperazinyl)-ethylamino]-benzoate
Methyl 4-Hydroxy-2-[N-picolinoyl-2-(1-phenyl-4-piperazinyl)-ethylamino]-benzoate
Methyl 5-Hydroxy-2-[N-picolinoyl-2-(1-phenyl-4-piperazinyl)-ethylamino]-benzoate
Methyl 6-Hydroxy-2-[N-picolinoyl-2-(1-phenyl-4-piperazinyl)-ethylamino]-benzoate Methyl 2-[N-(2-Pyridylmethyl)-2-(1-phenyl-4-piperazinyl)-ethylamino]-benzoate
Methyl 3-Amino-2-[N-(2-pyridylmethyl)-2-(1-phenyl-4-piperazinyl)-ethylamino]-benzoate
Methyl 4-Amino-2-[N-(2-pyridylmethyl)-2-(1-phenyl-4-piperazinyl)-ethylamino]-benzoate
Methyl 5-Amino-2-[N-(2-pyridylmethyl)-2-(1-phenyl-4-piperazinyl)ethylamino]-benzoate
Methyl 6-Amino-2-[N-(2-pyridylmethyl)-2-(1-phenyl-4-piperazinyl)-ethylamino]-benzoate
Methyl 3-Methoxy-2-[N-(2-pyridylmethyl)-2-(1-phenyl-4-piperazinyl)-ethylamino]-benzoate
Methyl 4-Methoxy-2-[N-(2-pyridylmethyl)-2-(1-phenyl-4-piperazinyl)-ethylamino]-benzoate
Methyl 5-Methoxy-2-[N-(2-pyridylmethyl)-2-(1-phenyl-4-piperazinyl)-ethylamino]-benzoate
Methyl 6-Methoxy-2-[N-(2-pyridylmethyl)-2-(1-phenyl-4-piperazinyl)-ethylamino]-benzoate
Methyl 3-Hydroxy-2-[N-(2-pyridylmethyl)-2-(1-phenyl-4-piperazinyl)-ethylamino]-benzoate
Methyl 4-Hydroxy-2-[N-(2-pyridylmethyl)-2-(1-phenyl-4-piperazinyl)-ethylamino]-benzoate
Methyl 5-Hydroxy-2-[N-(2-pyridylmethyl)-2-(1-phenyl-4-piperazinyl)-ethylamino]-benzoate
Methyl 6-Hydroxy-2-[N-(2-pyridylmethyl)-2-(1-phenyl-4-piperazinyl)-ethylamino]-benzoate
2-(1-Phenyl-4-piperazinylmethylamino)-benzoic acid
Methyl 2-(1-phenyl-4-piperazinylmethylamino)-benzoate
N-Benzyl-N-2-(1-phenyl-4-piperazinyl)-ethyl-o-aminophenyl-propionate
N-Benzyl-N-[1-methyl-2-(1-phenyl-4-piperazinyl)]-ethyl-o-aminophenyl propionate
N-Phenyl-N-2-(1-phenyl-4-piperazinyl)-ethyl-o-aminophenyl-propionate
N-Phenyl-N-[1-methyl-2-(1-phenyl-4-piperazinyl)]-ethyl-o-aminophenyl-proprionate Additional examples of compounds of Group A are as follows:

6-Hydroxy-1-[1-methyl-2-(1-phenyl-4-piperazinyl)-ethyl]-2-phenyl-1,2,3,4-tetrahydro-4-quinazolinone
6-Methoxy-1-[1-methyl-2-(1-phenyl-4-piperazinyl)-ethyl]-2-phenyl-1,2,3,4-tetrahydro-4-quinazolinone
1-[2-(4-morpholinyl)-ethyl]-2-phenyl-1,2,3,4-tetrahydro-4-quinazolinone
6-Amino-1-[2-(4-morpholinyl)-ethyl]-2-phenyl-1,2,3,4-tetrahydro-4-quinazolinone
2-Phenyl-1-[2-(4-thiomorpholinyl)-ethyl]-1,2,3,4-tetrahydro-4-quinazolinone
6-Amino-2-phenyl-1-[2-(4-thiomorpholinyl)-ethyl]-1,2,3,4-tetrahydro-4-quinazolinone
2-Phenyl-1-[2-(1-piperidinyl)-ethyl]-1,2,3,4-tetrahydro-4-quinazolinone
1-[2-(4-phenyl-1-piperidinyl)-ethyl]-2-phenyl-1,2,3,4-tetrahydro-4-quinazolinone
3-Methyl-1-[2-(4-phenol-1-piperidinyl)-ethyl]-2-phenyl-1,2,3,4-tetrahydro-4-quinazolinone
1-[1-Methyl-2-(4-phenyl-1-piperidinyl)-ethyl]-2-phenyl-1,2,3,4-tetrahydro-4-quinazolinone
6-Amino-1-[2-(4-phenyl-1-piperidinyl)-ethyl]-2-phenyl-1,2,3,4-tetrahydro-4-quinazolinone
6-Hydroxy-1-[2-(4-phenyl-1-piperidinyl)-ethyl]-2-phenyl-1,2,3,4-tetrahydro-4-quinazolinone
6-Methoxy-1-[2-(4-phenyl-1-piperidinyl)-ethyl]-2-phenyl-1,2,3,4-tetrahydro-4-quinazolinone
2-Methyl-1-[2-phenyl-1-piperidinyl)-ethyl]-1,2,3,4-tetrahydro-4-quinazolinone
6-Amino-2-methyl-1-[2-(4-phenyl-1piperidinyl)-ethyl]-1,2,3,4-tetrahydro-4-quinazolinone
2-(p-Hydroxyphenyl)-1-[2-(4-phenyl-1-piperidinyl)-ethyl]-1,2,3,4-tetrahydro-4-quinazolinone
6-Amino-2-(p-Hydroxyphenyl)-1-[2-(4-phenyl-1-piperidinyl)-ethyl]-1,2,3,4-quinazolinone
2-(p-Methoxyphenyl)-1-[2-(4-phenyl-1-piperidinyl)-ethyl]-1,2,3,4-tetrahydro-4-quinazolinone
6-Amino-2-(p-Methoxyphenyl)-1-[2-(4-phenyl-1-piperidinyl)-ethyl]-1,2,3,4-tetrahydro-4-quinazolinone
2-(p-Aminophenyl)-1-[2(4-phenyl-1-piperidinyl)-ethyl]-1,2,3,4-tetrahydro-4-quinazolinone
6-Amino-2-(p-Aminophenyl)-1-[2-(4-phenyl-1-piperidinyl)-ethyl]-1,2,3,4-tetrahydro-4-quinazolinone
2,2-Dimethyl-1-[2-(4-phenyl-1-piperidinyl)-ethyl]-1,2,3,4-tetrahydro-4-quinazolinone
1'-[2-(4-Phenyl-1-piperidinyl)-ethyl]-spiro(cyclobutane-1,2'-(1'H)-quinazolin)-4'(3'H)-one
1'-[2-(4-Phenyl-1-piperidinyl)-ethyl]-spiro(cyclopentane-1,2'-(1'H)-quinazolin)-4'(3'H)-one
1-[2-(4-Methyl-1-piperidinyl)-ethyl]-2-phenyl-1,2,3,4-tetrahydro-4-quinazolinone
3-Methyl-1-[2-(4-methyl-1-piperidinyl)-ethyl]-2-phenyl-1,2,3,4-tetrahydro-4-quinazolinone
1-[1-Methyl-2-(4-methyl-1-piperidinyl)-ethyl]-2phenyl-1,2,3,4-tetrahydro-4-quinazolinone
6-Amino-1-[2-(4-methyl-1-piperidinyl)-ethyl]-2-phenyl-1,2,3,4-tetrahydro-4-quinazolinone
6-Hydroxy-1-[2-(4-methyl-1-piperidinyl)-ethyl]-2-phenyl-1,2,3,4-tetrahydro-4-quinazolinone
6-Methoxy-1-[2-(4-methyl-1-piperidinyl)-ethyl]-2-phenyl-1,2,3,4-tetrahydro-4-quinazolinone
2-Methyl-1-[2-(4-methyl-1-piperidinyl)-ethyl]-1,2,3,4-tetrahydro-4-quinazolinone
6-Amino-2-methyl-1-[2-(4-methyl-1-piperidinyl)-ethyl]-1,2,3,4-tetrahydro-4-quinazolinone
2-(p-Hydroxyphenyl)-1-[2-(4-methyl-1-piperidinyl)-ethyl]-1,2,3,4-tetrahydro-4-quinazolinone
6-Amino-2-(p-Hydroxyphenyl)-1-[2-(4-methyl-1-piperidinyl)-ethyl]-1,2,3,4-tetrahydro-4-quinazolinone
2-(p-Methoxyphenyl)-1-[2-(4-methyl-1-piperidinyl)-ethyl]-1,2,3,4-tetrahydro-4-quinazolinone
6-Amino-2-(p-Methoxyphenyl)-1-[2-(4-methyl-1-piperidinyl)-ethyl]-1,2,3,4-tetrahydro-4-quinazolinone
2-(p-Aminophenyl)-1-[2-(4-methyl-1-piperidinyl)-ethyl]-1,2,3,4-tetrahydro-4-quinazolinone
6-Amino-2-(p-Aminophenyl)-1-[2-(4-methyl-1-piperidinyl)-ethyl]-1,2,3,4-tetrahydro-4-quinazolinone
2,2-Dimethyl-1-[2-(4-methyl-1-piperidinyl)-ethyl]-1,2,3,4-tetrahydro-4-quinazolinone
1'-[2-(4-Methyl-1-piperidinyl)-ethyl]-spiro(cyclobutane-1,2'(1'H)-quinazolin)-4'(3'H)-one
1'-[2-(4-Methyl-1-piperidinyl)-ethyl]-spiro(cyclopentane-1,2'(1'H)-quinazolin)-4'(3'H)-one
1-[2-(4-Hydroxy-4-phenyl-1-piperidinyl)-ethyl]-2-phenyl-1,2,3,4-tetrahydro-4-quinazolinone
1-[2-(4-Acetoxy-4-phenyl-1-piperidinyl)-ethyl]-2-phenyl-1,2,3,4-tetrahydro-4-quinazolinone
1-[2-(4-Phenyl-4-propoxy-1-piperidinyl)-ethyl]-2-phenyl-1,2,3,4-tetrahydro-4-quinazolinone
1-[2-(4-Butoxy-4-phenyl-1-piperidinyl)-ethyl]-2-phenyl-1,2,3,4-tetrahydro-4-quinazolinone 1-[2-(4-Isobutoxy-4-phenyl-1-piperidinyl)-ethyl]-2-phenyl-1,2,3,4-tetrahydro-4-quinazolinone
6-Hydroxy-1-[2-(4-hydroxy-4-phenyl-1-piperidinyl)-ethyl]-2-phenyl-1,2,3,4-tetrahydro-4-quinazolinone
6-Amino-1-[2-(4-hydroxy-4-phenyl-1-piperidinyl)-ethyl]-2-phenyl-1,2,3,4-tetrahydro-4-quinazolinone
6-Methoxy-1-[2-(4-hydroxy-4-phenyl-1-piperidinyl)-ethyl]-2-phenyl-1,2,3,4-tetrahydro-4-quinazolinone
2-(p-Hydroxyphenyl)-1-[2-hydroxy-4phenyl-1-piperidinyl)-ethyl]-1,2,3,4-tetrahydro-4-quinazolinone
1-[2-(4-Hydroxy-4-phenyl-1-piperidinyl)-ethyl]-2-(p-methoxy-phenyl)-1,2,3,4-tetrahydro-4-quinazolinone
2-(p-Aminophenyl)-1-[2-(4-hydroxy-4-phenyl-1-piperidinyl)-ethyl]-1,2,3,4-tetrahydro-4-quinazolinone
6-Amino-1-[2-(4-acetoxy-4-phenyl-1-piperidinyl)-ethyl]-2-phenyl-1,2,3,4-tetrahydro-4-quinazolinone
6-Amino-1-[2-(4-propoxy-4-phenyl-1-piperidinyl)-ethyl]-2-phenyl-1,2,3,4-tetrahydro-4-quinazolinone
6-Amino-1-[2-butoxy-4-phenyl-1-piperidinyl)-ethyl]-2-phenyl-1,2,3,4-tetrahydro-4-quinazolinone
2-(p-Aminophenyl)-1-[2-(4-acetoxy-4-phenyl-1-piperidinyl)-ethyl]-1,2,3,4-tetrahydro-4-quinazolinone
2-(p-Aminophenyl-1-[2-(4-propoxy-4-phenyl-1-piperidinyl)-ethyl]-1,2,3,4-tetrahydro-4-quinazolinone
2-(p-Aminophenyl)-1-[2-(4-butoxy-4-phenyl-1-piperidinyl)-ethyl]-1,2,3,4-tetrahydro-4-quinazolinone
6-Methoxy-1-[2-(4-propoxy-4-phenyl-1-piperidinyl)-ethyl]-2-phenyl-1,2,3,4-tetrahydro-4-quinazolinone
6-Hydroxy-1-[2-(4-propoxy-4-phenyl-1-piperidinyl)-ethyl]-2-phenyl-1,2,3,4-tetrahydro-4-quinazolinone
1-[2-(4-Acetoxy-4-phenyl-1-piperidinyl)-1-methyl-ethyl]-2-phenyl-1,2,3,4-tetrahydro-4-quinazolinone
1-[1-Methyl-2-(4-propoxy-4-phenyl-1-piperidinyl)-ethyl]-2-phenyl-1,2,3,4-tetrahydro-4-quinazolinone
2-(p-Aminophenyl)-1-[1-methyl-2-(4-propoxy-4-phenyl-1-piperidinyl)-ethyl]1,2,3,4-tetrahydro-4-quinazolinone
6-Amino-1-[1-methyl-2-(4-propoxy-4-phenyl-1-piperidinyl)-ethyl]-2-phenyl-1,2,3,4-tetrahydro-4-quinazolinone
6-Hydroxy-1-[1-methyl-2-(4-propoxy-4-phenyl-1-piperidinyl)-ethyl]-2-phenyl-1,2,3,4-tetrahydro-4-quinazolinone
6-Methoxy-1-[1-methyl-2-(4-Propoxy-4-phenyl-1-piperidinyl)-ethyl]-2-phenyl-1,2,3,4-tetrahydro-4-quinazolinone
1-[2-(1-[1-Methyl-2-phenethyl]-4-piperidinyl)-ethyl]-2-phenyl-1,2,3,4-tetrahydro-4-quinazolinone
1-[2-(1-[1-Methyl-2-phenethyl]-4-piperazinyl)-ethyl]-2-methyl-1,2,3,4-tetrahydro-4-quinazolinone
2-Benzyl-2-methyl-1-[2-(1-phenyl-4-piperazinyl)-ethyl]-1,2,3,4-tetrahydro-4-quinazolinone Additional examples of compounds of Group B are as follows:

2-[2-(4-Morpholinyl)-ethylamino]-benzamide
5-Amino-2-[2-(4-morpholinyl)-ethylamino]-benzamide
2-[2-(4-Thiomorpholinyl)-ethylamino]-benzamide
5-Amino-2-[2-(4-thiomorpholinyl)-ethylamino]-benzamide
2-[2-(1-Piperidinyl)-ethylamino]-benzamide
2-[2-(4-Phenyl-1-piperidinyl)-ethylamino]-benzamide
N-Methyl-2-[2-(4-phenyl-1-piperidinyl)-ethylamino]-benzamide
2-[1-Methyl-2-(4-phenyl-1-piperidinyl)-ethylamino]-benzamide
5-Amino-2-[2-(4-phenyl-1-piperidinyl)-ethylamino]-benzamide
5-Hydroxy-2-[2-(4-phenyl-1-piperidinyl)-ethylamino]-benzamide
5-Methoxy-2-[2-(4-phenyl-1-piperidinyl)-ethylamino]-benzamide
2-[2-(4-Methyl-1-piperdinyl)-ethylamino]-benzamide
N-Methyl-2-[2-(4-methyl-1-piperidinyl)-ethylamino]-benzamide
2-[1-Methyl-2-(4-methyl-1-piperidinyl)-ethylamino]-benzamide
5-Amino-2-[2-(4-methyl-1-piperidinyl)-ethylamino]-benzamide
5-Hydroxy-2-[2-(4-methyl-1-piperidinyl)-ethylamino]-benzamide
5-Methoxy-2-[2-(4-methyl-1-piperidinyl)-ethylamino]-benzamide
2-[2-(4-Hydroxy-4-phenyl-1-piperidinyl)-ethylamino]-benzamide
2-[2-(4-Acetoxy-4-phenyl-1-piperidinyl)-ethylamino]-benzamide
2-[2-(4-Phenyl-4-propoxy-1-piperidinyl)-ethylamino]-benzamide
2-[2-(4-Butoxy-4-phenyl-1-piperidinyl)-ethylamino]-benzamide
2-(4-Isobutoxy-4-phenyl-1-piperidinyl)-ethylamino]-benzamide
5-Hydroxy-2-[2-(4-hydroxy-4-phenyl-1-piperidinyl)-ethylamino]-benzamide
5-Amino-2-[2-(4-hydroxy-4-phenyl-1-piperidinyl)-ethylamino]-benzamide
2-[2-(4-Hydroxy-4-phenyl-1-piperidinyl)-ethylamino]-5-methoxy-benzamide
5-Amino-2-[2-(4-acetoxy-4-phenyl-1-piperidinyl)-ethylamino]-benzamide
5-Amino2-[2-(4-phenyl-4-propoxy-1-piperidinyl)-ethylamino]-benzamide
5-Amino-2-[2-(4-butoxy-4-phenyl-1-piperidinyl)-ethylamino]-benzamide
5-Methoxy-2-[2-(4-phenyl-4-propoxy-1-piperidinyl)-ethylamino]-benzamide
5-Hydroxy-2-[2-(4-phenyl-4-propoxy-1-piperidinyl)-ethylamino]-benzamide
2-[2-(4-Acetoxy-4-phenyl-1-piperidinyl)-1-methyl-ethylamino]-benzamide
5-[1-Methyl-2-(4-phenyl-4-propoxy-1-piperidinyl)-ethylamino]-benzamide
5-Amino-2-[1-methyl-2-(4-phenyl-4-propoxy-1-piperidinyl)-ethylamino]benzamide
5-Methoxy-2-[1-methyl-2-(4-phenyl-4-propoxy-1-piperidinyl)-ethylamino]-benzamide
5-Hydroxy-2-[1-methyl-2-(4-phenyl-4-propoxy-1-piperidinyl)-ethylamino]benzamide
2-[2-(1-[1-Methyl-2-phenethyl]-4-piperazinyl)-ethylamino]-benzamide If desired the above described compounds may be transformed into their acid addition salts, or quaternary ammonium salts by customary methods. For instance the acid addition salts may be obtained by dissolving the free base in a suitable solvent and acidifying the solution with the desired acid. Suitable pharmacologically effective acid addition salts include the sulfates, hydrochlorides, phosphates, cyclohexyl sulfamates, maleates, citrates, tartrates, succinates, ethane disulfomates, methane, sulfonates, isethionates, and the resinates obtained by reacting the amine group of the compound with a cation exchange resin such as a sulfonic, carboxylic, or phosphoric acid cation exchange resin.

To prepare a quaternary ammonium salt the free base is merely reacted with a suitable quaternizing agent, such as an alkyl halide, an aralkyl halide or dialkyl sulfate, preferably in the presence of an inert organic acid.

The following working examples further illustrate the invention.

EXAMPLE I

Preparation of
2-[2-(4-[1-Phenyl]piperazinyl)ethylamino]-benzamide
(730-372)

| 1-Phenyl-4-(2-hydroxyethyl)piperazine | |
|---|---|
| Step 1: N-Phenylpiperazine | 519 gms. |
| Ethylene oxide | 179 gms. |
| Methanol (absolute) | 800 ml. |

Charged phenylpiperazine and methanol, cooled to 0° to −10° and added the ethylene oxide over 1½ hours. (Rate of addition is not important.) Removed cooling bath and allowed temperature to rise to 40°, cooling to keep below 40° until temperature stops rising. Heated at 65° for 1½ hours, and added the methanol solution to hot heptane (gradually). Methanol was azeotroped out, adding heptane to keep the volume at 10 liters. Decanted from the insoluble oil and cooled to room temperature to give 336 gms., m.p. 79°–80.5°, plus a hard mass which apparently resulted from initial oiling out and then crystallization of the oil. This was extracted with hot heptane to give another 119 gms. of product. Yield=69%.

| 1-Phenyl-4-(2-hydroxyethyl)piperazine hydrochloride | |
|---|---|
| Step 2: 1-Phenyl-4-(2-hydroxyethyl)piperazine | 335 gms. |
| Methanol (anhydrous) | 1075 ml. |

HCl gas was bubbled into a solution of the 1-Phenyl-4-(2-hydroxyethyl)piperazine in methanol until the mixture was acidic, cooling to keep the temperature below 30°. The solid was filtered, washed with methanol and air dried to give 202 gms., m.p. 151°–155°. The mother liquor was used to dissolve 119 gms. of 1-Phenyl-4-(2-hydroxyethyl)piperazine and the solution acidified as above to give 179 gms., m.p. 153°–186°. Concentration of the mother liquor gave 116 gms., crop 2, m.p. 150°–152°. Yield=92.7%.

| 1-Phenyl-4-(2-chloroethyl)piperazine dihydrochloride | |
|---|---|
| Step 3: 1-Phenyl-4-(2-hydroxyethyl)piperazine HCL | 200 gms. |
| Chloroform | 1450 ml. |
| Thionyl chloride | 110 ml. |

The HCl salt was suspended in chloroform and thionyl chloride added over 1½ hours. The reaction mixture was refluxed 6 hours, cooled to room temperature, filtered and washed solid with chloroform. The air dried product was recrystallized from 2.5 liters methanol to give 214 gms., m.p. 215°–218°. Yield=87%

| 2-[2-(4-[1-Phenyl] piperazinyl)ethylamino]benzamide | |
|---|---|
| Step 4: | |
| o-Aminobenzamide | 3260 gms. |
| 1-Phenyl-4-(2-chloroethyl)piperazine dihydrochloride | 6500 gms |
| Triethylamine | 7070 gms. |
| Diglyme | 75 L. |

The reaction was run in 10 portions. The above materials were heated at 150° for 24 hours, cooled to room temperature and the solid filtered and washed with diglyme. The filtrate was evaporated to dryness on the rotovap at about 70° C. The diglyme residue was stirred with 2L. isopropanol and the solid filtered and washed with isopropanol, then with ether. Combined solids were recrystallized from 40L. of about 80% EtOH -20% water to give 1561 gm., m.p. 161.5°–2.5°. Concentration of the filtrate to 10 L. gave a second crop of 587 gms. which was recrystallized to give 477 gms., m.p. 161.5°–2.3°.

EXAMPLE II

Preparation of
1-[2-(1-Phenyl-4-piperazinyl)ethyl]-2-phenyl-1,2,3,4-tetrahydro-4-quinazolinone (740-222)

| 2-[2-(4-[1-Phenyl] piperazinyl)ethylamino] benzamide | 1000 gms. |
|---|---|
| Benzaldehyde | 342 gms. |
| Step 1: Piperidine | 148 gms. |
| Ethanol | 9 L. |

Charged all starting materials and refluxed 24 hours. The reaction was run in 2 parts and the reaction mixtures combined, seeded and cooled to room temperature overnight. The solid was filtered and washed to give 960 gms. crude. The crude product was recrystalized from 7.2 L. benzene and the product was dried at 95°–120° and 2 mm pressure for 10 hours to give 550 gm., m.p. 142.5°–3.5°. Concentration of the benzene mother liquor gave a second crop of 235 gm. (before drying under vacuum).

EXAMPLE III

Preparation of
1-[2-(1-Phenyl-4-piperazinyl)-ethyl]-2-phenyl-4[1H]-quinazolinone hydrochloride To a solution of 16.2 gm. (0.05 M) of the substituted benzamide (III, prepared as in Example I, Step 4) in 200 ml. of pyridine, 7.73 ml. (0.055M) of benzoyl chloride was added dropwise at 15°. The solution was refluxed for 2 hours and cooled to room temperature, and the solid formed was filtered off. It was recrystallized from 275 ml. of hot water to yield 10 gm. (44%) of white solid melting at 260°–262° C.

Preparation of
1-[2-(1-Phenyl-4-piperazinyl)-ethyl]-2-phenyl-1,2,3,4-tetrahydro-4-quinazolinone The free base of the above material was liberated, and 2.5 gm. (0.0061M) of this and 0.3 gm. (0.0022M) of aluminum chloride were put into 120 ml. of diglyme. To this was added 0.29 gm. (0.0076 M) of sodium borohydride in 30 ml. of diglyme, dropwise over 15 minutes at room temperature.

The temperature was brought to 85° and kept there for 1 hour, and then the solution was cooled to 20° in an icebath and 20 ml. of water was added along with enough hydrochloric acid to bring the pH to 5.

The clear solution was taken down on the rotovap to give a yellow solid, which was triturated with cold water and filtered to give 3.2 gm. of white solid, melting at 268°–270° (decomp.).

1.0 gm. of the solid was freed from its salt form and recrystallized from 10 ml. of benzene to yield, after drying overnight at 95°, 0.25 gm. of white solid, melting at 142°–143° C. A mixed melting point with an authentic sample of 740-222 showed no depression.

EXAMPLE IV

2-[2-(4-[1-Phenyl] piperazinyl) ethylamino] benzamide cyclohexyl sulfamate

| | |
|---|---|
| 2-[2-(4-[1-Phenyl] piperazinyl) ethylamino] benzamide | 15.2 gms |
| Cyclohexylsulfamic acid | 9.0 gms. |
| Tetrahydrofuran | 300 . ml. |

The benzamide was dissolved in about 250 ml. tetrahydrofuran and a solution of cyclohexylsulfamic acid in about 50 ml. tetrahydrofuran was added. The solid which precipitated was filtered, washed, and dried and then recrystallized from a mixture of 600 ml. isopropanol, 100 ml. methanol, and 10 drops of 10% NaOH to give 13 gms., m.p. 152°-4°.

EXAMPLE V

Preparation of
2-[2-(4-[1-Phenyl] piperazinyl) ethylamino] benzamide phosphate

| | |
|---|---|
| 2-[2-(4-1-Phenyl] piperazinyl) ethylamino] benzamide | 90 gm.s |
| Phosphoric acid (85%) | 45 ml. |
| Ethanol (95) | 450 ml. |

The benzamide was suspended in ethanol and a mixture was 45 ml. phosphoric acid in 225 ml. was added. The mixture was stirred, heated to solution, filtered, and left overnight. The solid product was filtered, washed with ethanol, dried, and recrystallized from 450 ethanol and 240 ml. water to give 64 gms., m.p. 185°–6.5°.

EXAMPLE VI

Preparation of
2-[2-(4-1-Phenyl] piperazinyl) ethylamino] benzamide hydrochloride

| | |
|---|---|
| 2-[2-(4-[1-Phenyl] piperazinyl) ethylamino] benzamide | 250 gms. |
| Ethanol 95% | 4 l. |
| HCl concentrated | 71 ml. |

A solution of 71 ml. concentrated HCl in 213 ml. water was added to a hot solution of the benzamide in 4 l. of ethanol. The mixture was cooled to 30° and the solid filtered, washed with alcohol, and dried over $P_2O_5$ under vacuum to give 249 gms., m.p. 257.5°–60° (dec.).

EXAMPLE VII

Preparation of
2-[-(1-[p-Methoxyphenyl]-4-piperazinyl) ethylamino] benzamide (751-295)

| 1-(p-Methoxyphenyl)-4-(2-hydroxyethyl) piperazine hydrochloride | |
|---|---|
| Step 1:  1-(p-Methoxyphenyl) piperazine | 26.5 gms. |
| Methanol (absolute) | 100. ml. |
| Ethylene oxide | 7.35 gms. |

1-(p-Methoxyphenyl) piperazine was dissolved in methanol and ethylene oxide added at −20°. The mixture was stirred while warming up to room temperature (1 hour), 2½ hours at room temperature, and 1 hour at 35°. An additional 1 ml. ethylene oxide was added, the mixture was stirred 1 hour at 50° and cooled. To the reaction mixture was added 75 ml. of a solution of HCl in methanol containing 10 gms. HCl in 100 ml. Ether (200 ml.) was added and the solid filtered after 1 hour to give 30 gms. product which was used without further purification.

| 1-(p-Methoxyphenyl)-4-(2-chloroethyl) piperazine dihydrochloride | |
|---|---|
| Step 2:  1-(p-Methoxyphenyl)-4-(2-hydroxyethyl) piperazine hydrochloride | 30 gms. |
| Chloroform | 500 ml. |
| Thionyl chloride | 33 gms. |

The HCl salt was suspended in chloroform and thionyl chloride added dropwise, at room temperature, over 1 hour. The reaction mixture was refluxed 8 hours, stirred 12 hours at room temperature. The solid was filtered and recrystallized from 180 ml. MeOH and 40 ml. ether to give 24.5 gms., m.p. 220°–8°.

| 2[2-1-[p-Methoxyphenyl]-4-piperazinyl) ethylamino] benzamide | |
|---|---|
| Step 3:  1-(p-Methoxyphenyl)-4-(2-chloroethyl) piperazine dihydrochloride | 24 gms. |
| o-Aminobenzamide | 10 gms. |
| Triethylamine | 30.7 ml. |
| Diglyme | 250 ml. |

All starting materials were combined and heated at 150° for 96 hours. The reaction mixture was cooled, filtered, and the filtrate concentrated on the rotovap. The residue was triturated with 200 ml. isopropanol, filtered, and the solid recrystallized from 300 ml. 80% ethanol and then from a mixture of 60 ml. dimethylformamide and 100 ml. water to give 7.8 gms., m.p. 170°–2°

EXAMPLE VIII

Preparation of
1-[2-(1-Phenyl-4-piperazinyl ethyl]-2-phenyl-1,2,3,4-tetrahydro-4-quinazolinone hydrochloride

| | |
|---|---|
| 1-[2-(1-Phenyl-4-piperazinyl ethyl]-2-phenyl-1,2,3,4-tetrahydro-4-quinazolinone | 10 gms. |
| Ethanol 95% | 100 ml. |

The base was dissolved in ethanol and 10 ml. of 2.5N HCl was added. After several hours the solid was filtered, washed with ethanol, and dried over $P_2O_5$ to give 100% yield of the HCl salt, m.p. 267°–71° (dec.).

EXAMPLE IX

Preparation of
1-[2-(1-Phenyl-4-piperazinyl) ethyl]-2-methyl-1,2,3,4-tetrahydro-4-quinazolinone hydrochloride

| | |
|---|---|
| 2-[2-(4-[1-Phenyl] piperazinyl) ethylamino] benzamide | 32.4 gms. |
| Acetic acid, glacial | 200 ml. |
| 1,1-Dimethoxyethane | 12.2 ml. |

The benzamide was dissolved in acetic acid, dimethoxyethane added and 3.5 ml. concentrated sulfuric acid added dropwise. The reaction mixture was stirred 5 hours, left overnight at room temperature, concentrated on the rotovap, and 75 ml. water added to the residue. The solution was made alkaline with 10% NaOH and extracted with benzene. The benzene extract was washed with water, dried, and concentrated to dryness. The benzene residue was dissolved in 90 ml. benzene and 100 ml. hexane was added to give 32 gms. crystalline material. This was suspended in 50 ml. 95% ethanol, 25 ml. 2.5N HCl added and heated to solution. A few more ml. 2.5N HCl was added, the solution treated with charcoal and cooled to give 30.5 gms. of the HCl salt. This was recrystallized twice from a 84% ethanol—16% water mixture to give 18.5 gms., m.p. 242°-8° (2.05% water of hydration).

EXAMPLE X

Preparation of
1'-[2-(1-Phenyl-4-piperazinyl) ethyl]-1-methylspiro-[piperidine-4,2'(1'H) quinazolin]-4' (3'H)-one sulfate

| | |
|---|---|
| 2-[2-(4-[1-Phenyl] piperazinyl) ethylamino] benzamide | 19.4 gms. |
| Acetic acid, glacial | 120 ml. |
| 1-Methyl-4-piperidone | 12 ml. |

The benzamide was dissolved in acetic acid, 1-methyl-4-piperidone added and then 1.3 ml. sulfuric acid added dropwise. The reaction mixture was stirred 3 hours at room temperature, left over the weekend at room temperature, and heated 5 hours at 90°. 1-Methyl-4-piperidone (2 ml.) was added, the reaction mixture heated 7 hours at 90°, left overnight at room temperature and concentrated on the rotovap. The residue was dissolved in 150 ml. water. After several hours the solid was filtered off. The crude product was recrystallized twice from water and dried over $P_2O_5$ to give 11 gms. product, m.p. indefinite (starts at 160°), which contained 5% water of crystallization.

EXAMPLE XI

2-[N-(β-4-Morpholinoethyl)amino]benzamide. (730-310)

A mixture of 27.2 g 2-aminobenzamide and 18.6 g N-(2-chloroethyl)-morpholine hydrochloride was heated 24 hours at 130°-40°, cooled to room temperature, stirred with water, filtered, the filtrate made alkaline with 50% NaOH and extracted with chloroform. The chloroform was dried, concentrated to dryness and the residue recrystallized from 60 ml methanol to give 17 g product, m.147-9.

| | C | H | N |
|---|---|---|---|
| Calcd. | 62.65 | 7.63 | 16.87 |
| Found | 62.61 | 7.43 | 17.16 |

EXAMPLE XII

Methyl 2-[2-(1-phenyl-4-piperazinyl)ethylamino]benzoate. (756-267)

A mixture of 17.6 methyl anthranilate, 35.6 g 1-(2-chloroethyl)-4-phenylpiperazinyl dihydrochloride, 17.4 g sodium acetate, and 50 ml water was refluxed 24 hours, cooled, 60 ml water and 60 ml NH$_4$OH was added and extracted with chloroform. The chloroform was dried and concentrated and the residue recrystallized from ethyl acetate to give 10.6 g., m.104-6. This was recrystallized from 250 ml isopropyl ether and converted to the HCl salt which was recrystallized from water and converted back to the base.

| | C | H | N |
|---|---|---|---|
| Calcd. | 70.77 | 7.43 | 12.38 |
| Found | 71.12 | 7.56 | 12.44 |

EXAMPLE XIII

Methyl-2-[2-(1-phenyl-4-piperazinyl)ethylamino]benzoate hydrochloride. (762-313)

A mixture of 106.8 g 1-(2-chloroethyl)-4-phenylpiperazine dihydrochloride, 52.8 g methyl anthranilate, 52.2 g sodium acetate, and 150 ml water was refluxed 24 hours, cooled, 180 ml water and 180 ml concentrated NH$_4$OH added and extracted with chloroform. The chloroform residue was recrystallized from ethyl acetate to give 30.2 g base which was chromatographed on silica and recrystallized from 1.2 liters methanol to give 28.3 g., m.105-8. A portion of this (12 g) was added to 850 ml hot water, 10 ml concentrated HCl added, filtered and cooled to give 9.8 g product, m.213-18.5.

| | C | H | N | Cl |
|---|---|---|---|---|
| Calcd. | 63.91 | 6.97 | 11.18 | 9.43 |
| Found | 63.65 | 7.16 | 11.26 | 9.19 |

EXAMPLE XIV

Preparation of
2-[2-(4-phenyl-1-piperazinyl)propylamino]benzamide hydrochloride. (762-381)

2-Aminobenzamide (75g), 138 g sodium acetate, 174 g 1-(2-chloropropyl)-4-phenylpiperazine dihydrochloride, and 455 ml water were refluxed 4 hrs and cooled overnight. The mixture was extracted with CHCl$_3$, the CHCl$_3$ extract washed with water and dried and concentrated to dryness. The CHCl$_3$ residue was recrystallized from 1800 ml alcohol to give 38 g solid. This was crystallized twice from alcohol to give 22.4 g, m.196-815. A portion of this (10 g) was dissolved in hot alcohol, treated with 3N HCl, cooled and filtered to give 8.5 g product, m.258-61.

|         | C     | H    | N     |
|---------|-------|------|-------|
| Calcd.  | 64.07 | 7.26 | 14.94 |
| Found   | 63.81 | 7.23 | 14.58 |

EXAMPLE XV

Preparation of 2-(2-[4-phenyl-1-piperazinyl]ethylamino)-N-methylbenzamide. (763-423)

N-Methylanthranilamide (14 g), 28 g 1-(2-chloroethyl)-4-phenylpiperazine hydrochloride, 17.5 g sodium acetate and 100 ml water were refluxed 24 hrs, 100 ml water and 100 ml conc NH$_4$OH added and the solid filtered and dissolved in 125 ml hot 60% ethanol. After stirring for 4 days, the solid was filtered to give 15 g, m.98–100. The solid was dissolved in 800 ml dry ether and acidified with dry HCl gas dissolved in ether. The solid as filtered and dried to give the HCl salt.

|         | C     | H    | N     |
|---------|-------|------|-------|
| Calcd.  | 51.54 | 6.71 | 12.04 |
| Found   | 51.14 | 6.61 | 12.38 |

EXAMPLE XVI

Preparation of N-(2-[2-(1-phenyl-4-piperazinyl)ethylamino]benzoyl) morpholine hydrochloride. (763-431)

o-Aminobenzoylmorpholine (9 g), 14 g phenylpiperazinoethyl chloride hydrochloride, 12 g sodium acetate, and 50 ml water were refluxed 24 hours. The reaction was cooled to 30°, 100 ml water 100 ml NH$_4$OH added and the liquid decanted. The solid was stirred with 125 ml hot 60% propanol and filtered. The solid was dissolved in 1 liter of ether and 120 ml methanol and a solution of HCl gas in ether added to give 6.1 g, m.143-5.

|        | C     | H    | N     | Cl   |
|--------|-------|------|-------|------|
| Calcd  | 64.10 | 7.25 | 13.00 | 8.23 |
| Found  | 63.98 | 7.00 | 12.73 | 8.19 |

EXAMPLE XVII

Preparation of 2-[2-(4-phenethyl-1-piperazinyl)ethylamino]benzamide hydrochloride. (763-463)

A mixture of 13.6 g anthranilamide, 34.5 g 4-phenethylpiperazinoethyl chloride dihydrochloride, 17.5 g sodium acetate, and 50 ml water was refluxed for 24 hours, 50 ml water and 50 ml NH$_4$OH was added and the mixture cooled. The liquid was decanted and the oily solid dissolved in 100 ml propanol, 200 ml water added and the solid filtered. The solid was dissolved in 2 liters of dry ether, acidified with dry HCl gas and filtered. The HCl salt was recrystallized from propanol to give 9.2 g product.

|        | C     | H    | Cl    | N     |                        |
|--------|-------|------|-------|-------|------------------------|
| Calcd. | 53.57 | 6.85 | 22.59 | 11.90 | (for ½ mole H$_2$O)    |
| Found  | 53.92 | 6.97 | 22.41 | 12.11 |                        |

EXAMPLE XVIII

Preparation of 5-Methoxy-2-(2[4-phenyl-1-piperazinyl]ethylamino)-benzamide. (765-381)

A mixture of 45.7 g 5-methoxyanthranilamide hydrochloride, 63 g 4-phenyl-1-piperazinylethyl chloride dihydrochloride, 82 g anhydrous sodium acetate, and 240 ml water was refluxed for 24 hrs, cooled to 60°, 250 ml water added, cooled to room temperature and filtered to give 64 g solid, m.246-7.5. A 7.5 g portion was put into 50 ml methanol and HCl gas added for about 1½ min (most of material dissolved). Another 100 ml methanol was added and the mixture refluxed to dissolve the solid, then filtered, cooled, and diluted with an equal volume of ether which gave a mixture of crystalline solid and tarry product. The crystalline slurry was decanted and diluted with 400 ml ether. The tarry product was dissolved in 200 ml methanol and added to the first portion. The solid was filtered and dried to give 8.0 g solid which softened at 148° and puffed up at 160°.

|        | C     | H    | Cl   | N     |
|--------|-------|------|------|-------|
| Calcd  | 61.45 | 6.96 | 9.07 | 14.33 |
| Found  | 61.66 | 7.12 | 9.21 | 14.35 |

EXAMPLE XIX

5-Nitro-2-(2-[4-phenyl-1-piperazinyl]ethylamino)benzamide. (769-829)

Step 1. 1-(2-Aminoethyl)-4-phenylpiperazine

A solution of 600 g 1-Cyanomethyl-4-phenylpiperazine in 1525 ml tetrahydrofuran was added dropwise to a suspension of 181 g LiAlH$_4$ in 4.5 liters tetrahydrofuran. The mixture was refluxed 18 hours, cooled and added 181 ml water, 181 ml 15% NaOH, and 543 ml water. The mixture was filtered and concentrated to dryness on the rotovap and the residue distilled to give 470 g product, b0.1 117°–24°, m.50°–7°.

Step 2. 5-Nitro-2-(2-[4-phenyl-1-piperazinyl]ethylamino)benzoic acid.

2-Chloro-5-nitrobenzoic acid (179 g), 182.5 g 1-(2-aminoethyl)-4-phenylpiperazine, 138 g K$_2$CO$_3$, 900 ml isoamyl alcohol and CuO catalyst were refluxed for 8 hours adding a pinch of CuO periodically. The mixture was cooled overnight, diluted with butanol and filtered. The solid was dissolved in water and neutralized to pH 4–4.5 with 3N HCl to give 247 g crude product. This was recrystallized from 3.5 liters dimethylformamide and 1 liter of water to give 220 g product, m.243–6.

Step 3. 5-Nitro-2-(2-[4-phenyl-1-piperazinyl]ethylamino)benzamide

A solution of 7.4 g 5-nitro-2-(2-[4 -phenyl-1-piperazinyl]ethylamino)-benzoic acid in 80 ml tetrahydrofuran was treated with 2.8 ml triethylamine, stirred 5minutes, 1.6 ml ethyl chloroformate added, stirred 15 minutes, 80 ml NH₄OH added and stirred 30 minutes. After addition of 70 ml water, the mixture was concentrated on the rotovap at 70° to a slurry which was heated to boiling and filtered hot to give 6.7 g solid. This was boiled with 70 ml water and 2.5 ml 45% KOH, filtered hot and washed with hot water to give 3.2 g product, m.209–10.

|        | C     | H    | N     |
|--------|-------|------|-------|
| Calcd. | 61.77 | 6.28 | 18.96 |
| Found  | 61.84 | 6.44 | 18.68 |

EXAMPLE XX 2-(2-[4-Benzyl-1-piperazinyl]ethylamino)benzamide trihydrochloride. (775-679)

Anthranilamide (35 g), 40 g 2-(4-benzyl-piperazine)ethyl chloride dihydrochloride (prepared from benzylpiperazine by reaction with ethylene oxide followed by chlorination of the product with thionyl chloride), 40 g sodium acetate and 400 ml water were refluxed 24 hours. The reaction mixture was poured into 500 ml water, made alkaline, and the solid filtered, washed and dried to give 24.5 g, m.142–6. This was recrystallized from methanol-ether to give 18.2 g solid which was dissolved in 50 ml methanol. The solution was made strongly acidic with dry HCl, heated to 50° and 100 ml chloroform and 100 ml methanol added. The resultant solid was filtered and recrystallized from 300 ml propanol to give the product.

|        | C     | H    | N     | Cl    |
|--------|-------|------|-------|-------|
| Calcd. | 53.64 | 6.53 | 12.51 | 23.75 |
| Found  | 52.36 | 6.77 | 11.67 | 23.73 |

EXAMPLE XXI

Preparation of 5-Amino-2-(2-[4-phenyl-1-piperazinyl]-ethylamino)benzamide hydrochloride. (776-074)

Step 1 -
5-Nitro-2-(2-[4-phenyl-1-piperazinyl]ethylamino)-benzoic acid.

2-Chloro-5-nitrobenzoic acid (179 g), 182.5 g 1-(2-aminoethyl)-4-phenylpiperazine, 138 g K₂CO₃ and 900 ml isoamyl alcohol were refluxed for 8 hrs with occasional addition of small amounts of CuO powder and cooled overnight, diluted with butanol and filtered. The solid was dissolved in water and neutralized to Congo red with 3N HCl to give 257 g solid. The was recrystallized from a mixture of 3.5 liters dimethylformamide and 1 liter of water to give 220 g product, m.243–6.

Step 2 -
5-Nitro-2-(2-[4-phenyl-1-piperazinyl]ethylamino)benzamide.

5-Nitro-2-(2-[4-phenyl-1-piperazinyl]ethylamino)benzoic acid. (7.4 g) in 80 ml tetrahydrofuran was stirred 5 min with 2.8 ml triethylamine. Ethyl chloroformate (1.6 ml) was added and the mixture stirred 15 min. Concentrated NH₄OH (80 ml) was added, the mixture stirred ½ hr, 70 ml water added and the mixture concentrated on the rotovap. The resultant aqueous slurry was boiled, filtered hot and the solid washed with hot water to give 6.7 g solid. This was boiled with 70 ml water and 2.5 ml 45% KOH, filtered and washed to give 3.2 g product, m.209–10.

Step 3 -
5-Amino-2-(2-[4-phenyl-1-piperazinyl]ethylamino)benzamide hydrochloride.

5-Nitro-2-(2-[4-phenyl-1-piperazinyl]ethylamino)benzamide hydrochloride (2.1 g) in 25 ml methanol was hydrogenated with 0.3 g 5% Pd/C catalyst. The catalyst was filtered and the filtrate diluted with ether to give 1.7 g product, m.212–13 (dec.).

|       | C     | H    | N     |
|-------|-------|------|-------|
| Calcd | 60.12 | 6.93 | 18.45 |
| Found | 59.86 | 6.87 | 18.33 |

EXAMPLE XXII

2-[2-(1-Phenyl-4-piperazinyl)ethylamino]-N-phenylbenzamide. (776-285)

Step 1. 2-Amino-N-phenylbenzamide.

Isatoic anhydride (130 g) and aniline (700 ml) were heated to 140°, cooled, poured into 20 liters of water and filtered. The solid was extracted with 4 liters of 1.25N HCl and filtered. The filtrate was washed with ether, made alkaline with 2.5N NaOH and filtered. The solid was treated with ether and water to give 120 g product.

Step 2.
2-[2-(1-Phenyl-4-piperazinyl)ethylamino]-N-phenylbenzamide.

2-Amino-N-phenylbenzamide (112 g) was refluxed 24 hours with 187 g 1-(2-chloroethyl)-4-phenylpiperazine, 197 g sodium acetate and 530 ml water, cooled, 500 ml water added, the mixture made basic with concentrated NH₄OH and extracted with chloroform. The chloroform was washed with water, dried and concentrated. The residue recrystallized from 350 ml alcohol gave 69.6 g. Part of this (20 g) was recrystallized from 500 ml alcohol and then from 375 ml alcohol to give 14.5 g., m.141–4.

|        | C     | H    | N     |
|--------|-------|------|-------|
| Calcd. | 74.97 | 7.05 | 13.99 |
| Found  | 74.64 | 6.94 | 14.01 |

EXAMPLE XXIII

2-[2-(1-[p-Hydroxyphenyl]-4-piperazinyl)ethylamino]-benzamide. (785-419)

Step 1.
1-(p-Methoxyphenyl)-4-(2-hydroxyethyl)piperazine.

1-(p-Methoxyphenyl)piperazine dihydrochloride (100 g) was slurried in 210 ml water, made alkaline with NaOH, extracted with ethyl acetate and the extract concentrated to give 69 g residue which was distilled to give 52.9 g, b 0.5 138°. The base was dissolved in 200 ml methanol and treated with 14.55 g ethylene oxide at −15°, stirred 4 hours at room temperature and 1 hour at 35°. Another 2 ml ethylene oxide was added, the mixture stirred 1 hour at 50°, cooled and concentrated to give 65 g solid.

Step 2.
1-(p-Hydroxyphenyl)-4-(2-bromoethyl)piperazine dihydrobromide.

1-(p-Methoxyphenyl)-4-(2-hydroxyethyl)piperazine (10 g) was refluxed 20 hours with 100 ml 48% HBr and concentrated as far as possible on the rotovap. The mixture was filtered and washed with acetone to give a solid which was recrystallized from alcohol to give the product.

|  | C | H | N |
|---|---|---|---|
| Calcd. | 32.24 | 4.28 | 6.27 |
|  | 32.43 | 4.37 | 6.62 |

Step 3.
2-[2-(1-[p-Hydroxyphenyl]-4-piperazinyl)ethylamino]-benzamide.

A mixture of 61 g 1-(p-hydroxyphenyl)-4-(2-bromoethyl)piperazine dihydrobromide, 18.5 g anthranilamide, 33.5 g sodium acetate, and 250 ml water was refluxed 16 hours, cooled, filtered and the solid washed with water and isopropanol. The solid was suspended in water and made alkaline with $Na_2CO_3$. The solid was filtered, suspended in 75% ethanol and added dilute HCl until acidic. The solution was cooled and the solid filtered and recrystallized from 1200 ml water to give 18.5 g product, m.285.

|  | C | H | N |
|---|---|---|---|
| Calc. | 60.55 | 6.69 | 14.86 |
| Found | 60.30 | 6.56 | 14.67 |

EXAMPLE XXIV

5-Ethoxy-2-(2-[4-phenyl-1-piperazinyl]ethylamino)benzamide. (791-935)

Step 1. 5-Hydroxy-2-nitrobenzoic acid.

5-Chloro-2-nitrobenzoic acid (100 g) in 800 ml dimethylsulfoxide was treated with 112 g powdered KOH with cooling, 170 ml anhydrous alcohol added and the mixture stirred 2 hours at 25° and then left overnight. The mixture was kept at 28° for about 8 hours, then overnight at 0°, warmed to room temperature and 3.5 liters of water added. The mixture was acidified with HCl, 1 kg NaCl added and extracted with ethyl acetate. The extract was washed with water, dried, 50 g $KHCO_3$ in 500 ml water added, diluted to 2 liters, and the ethyl acetate blown off with a stream of nitrogen. The solution was acidified and filtered to give 56 g product, m.128–30.

Step 2. Methyl 5-hydroxy-2-nitrobenzoate.

5-Hydroxy-2-nitrobenzoic acid (47 g) in 750 ml methanol was treated with 160 ml $BF_3$-ether, ether distilled off until pot temperature reached 60°, and refluxed overnight. The procedure was repeated with 100 ml $BF_3$-ether. The mixture was poured into 3 volumes of water, extracted with ethyl acetate, the ethyl acetate washed with water, $KHCO_3$ solution, water, dried and concentrated to give 48.4 g product.

Step 3. 5-Hydroxy-2-nitrobenzamide

Methyl 5-hydroxy-2-nitrobenzoate (48 g) in 340 ml methanol was heated 30 hours at 107° in a pressure vessel with 140 ml $NH_3$. The mixture was cooled and concentrated to dryness on the rotovap. Water was added (200 ml) and the solid filtered and dried to give 12 g product, m.135–8.

Step 4. 5-Hydroxyanthranilanide.

5-Hydroxy-2-nitrobenzamide (51 g) in 1 liter of methanol was reduced at 50 psi using 3 g of Pd-C catalyst. The mixture was filtered, concentrated to dryness, the residue shaken up with ether and filtered to give 38.3 g product, m.151–2.

Step 5. 5-Benzyloxyanthranilamide

A mixture of 5-hydroxyanthranilamide (15.2 g), 250 ml water, 5.1 ml 50% NaOH, and 11.7 ml benzyl chloride was heated ½ hour at 95°, filtered and the solid recrystallized from 200 ml butanol to give 16.6 g product, m.163–5.

Step 6.
5-Benzyloxy-2-(2-[4-phenyl-1-piperazinyl]ethylamino)-benzamide 1-(2-Chloroethyl)-4-phenylpiperazine dihydrochloride (3.3 g) was converted to the base and added to 1.2 g 5-Benzyloxyanthranilamide in 125 ml propanol. The solution was refluxed 3 hours, cooled, filtered, and the filtrate concentrated to dryness. The residue was chromatographed on alumina to give 0.63 g product.

Step 7.
5-Ethoxy-2-(2-[4-phenyl-1-piperazinyl]ethylamino)benzamide.

5-Benzyloxy-2-(2-[4-phenyl-1-piperazinyl]ethylamino)benzamide (1.8 g) in 35 ml ethanol was hydrogenated using 1 g 5% Pd-C catalyst. The mixture was heated to boiling and filtered. The filtrate was cooled and the solid filtered and washed to give 0.7 g product, m.142–3.

|  | C | H | N |
|---|---|---|---|
| Calcd. | 68.45 | 7.66 | 15.20 |
| Found | 68.12 | 7.57 | 14.90 |

EXAMPLE XXV

2-[2-(4-Hydroxy-4-phenylpiperidyl)ethylamino]benzamide. (776-246)

Step 1. o-Benzylaminobenzamide

To a hot solution of 20 g NaOH in 1250 ml water was added 68 g 2-aminobenzamide followed by 58 ml benzyl chloride. The mixture was refluxed 20 minutes, cooled and the solid filtered and washed with water. The product was recrystallized from 95% alcohol to give 62 g, m.169–73.

Step 2. 2-[Benzyl(2-hydroxyethyl)amino]benzamide.

o-Benzylaminobenzamide (62 g) was added to a cold solution of 85 ml ethylene oxide in 500 ml acetic acid, the mixture stirred 22 hours at room temperature and concentrated on the rotovap to remove 250 ml acetic acid. The remainder was made alkaline with 10% NaOH and the solid filtered washed with water and recrystallized from 300 ml ethyl acetate to give 48.5 g. product, m. 133–7.

Step 3. 2-[Benzyl(2-chloroethyl)amino]benzamide hydrochloride.

2-[Benzyl(2-hydroxyethyl)amino]benzamide (10 g) was added at 0° to 50 ml SOCl₂, stirred 7½ hours at room temperature and left overnight. The mixture was concentrated on the rotovap, ethyl acetate added and the solid filtered to give 11 g product, m.171-4.

Step 4.
2-[Benzyl-(2-[4-hydroxy-4-phenylpiperidyl]ethyl)amino]benzamide hydrochloride.

A mixture of 19.5 g 2-[Benzyl(2-chloroethyl)amino]benzamide hydrochloride, 15.75 g powdered anhydrous Na₂CO₃, 10.6 g 4-hydroxy-4-phenylpiperidine and 250 ml butanol was refluxed 20 hours, cooled and an equal volume of chloroform added. The mixture was filtered and the filtrate concentrated on the rotovap to dryness. The residue was dissolved in 500 ml ether, a little dry ice added, the mixture filtered and concentrated to dryness. The residue in 300 ml ether was treated with dry HCl and filtered to give 15 g product.

Step 5.
2-[2-(4-hydroxy-4-phenylpiperidyl)ethylamino]benzamide.

2-[-(2-Hydroxy-4-phenylpiperidyl]ethyl)amino]benzamide hydrochloride (12 g.) in 2:: ml methanol was hydrogenated at 60 psi using 1.5 g 5% Pd-C catalyst (1.5 g and 1.0 g portions of fresh catalyst were added during the reduction). The catalyst was filtered off and the filtrate concentrated to dryness on the rotovap. The residue was recrystallized from 60 ml isopropanol and then from 300 ml isopropanol to give 6.1 g product, m.108–13. Analysis showed 13.39% isopropanol in the product.

|  | C | H | N | Cl |
|---|---|---|---|---|
| Calcd. (uncorrected) | 64.08 | 6.72 | 11.21 | 9.46 |
| Found | 63.77 | 7.60 | 9.89 | 8.89 |

EXAMPLE XXVI

1-[2-(4-Hydroxy-4-phenylpiperidino)ethyl]-2-phenyl-1,2,3,4-tetrahydro-4-quinazolinone Methanesulfonate (776-278).

A mixture of 2-[2-(4-hydroxy-4-phenylpiperidino)ethylamino]benzamide (8 g), benzaldehyde (2.5 ml), piperidine (1.2 ml), and absolute ethanol (64 ml) was refluxed for 30 hours. The solvent was removed on a rotovap. The thick oil was redissolved in 80 ml absolute ethanol and the solution treated with methanesulfonic acid. Ether (80 ml) was added and after 1 hr the product was filtered. The product was recrystallized from 71.5% ethanol; yield 8.5 g, m.p. 252°–254° C.

|  | C | H | N | S |
|---|---|---|---|---|
| Calcd. | 64.03 | 6.33 | 7.85 | 6.12 |
| Found | 64.22 | 6.35 | 8.02 | 6.32 |

Preparation of 2-[2-(4-propionoxy-4-phenylpiperidyl)ethylamino]benzamide (776–262)

Step 1- o-Benzylaminobenzamide

A soln of 20 g sodium hydroxide in 1250 ml water was heated to near boiling and 68 g 2-aminobenzamide added. When the aminobenzamide dissolved, 58 g benzylchloride was added and the mixture refluxed for 20 min, cooled and filtered. The solid was recrystallized from 2-liters 95% alcohol to give 62 g product, m.169.5–73.

Step 2-2-[Benzyl(2-hydroxyethyl)amino]benzamide

To a cooled soln of 85 ml ethylene oxide in 500 ml acetic acid was added 62 g o-benzylaminobenzamide and the mixture stirred at room temp. for 22 hrs. 250 ml acetic acid was removed under vac and the mixture made alkaline, with cooling, with 10% NaOH. The solid was filtered, washed with water and recrystallized from 300 ml ethyl acetate to give 48.5 g product, m.137–7. Concentration of the mother liquid gave a 2nd crop of 13.4 g.

Step 3-2-[Benzyl(2-chloroethyl)amino]benzamide hydrochloride

2-[Benzyl(2-hydroxyethyl)amino]benzamide (10 g) was added to 50 ml SOCl₂ at 0° and the mixture stirred 7½ hrs at room temperature, then left at room temperature overnight. SOCl₂ was removed under vac at room temperature and the residue stirred with ethyl acetate and filtered. The solid was washed with ethyl acetate to give 11 g product, m.174-4.

Step 4-2-[Benzyl-(2-[4-hydroxy-4-phenylpiperidyl]ethyl)amino]benzamide

2-[Benzyl(2-chlorethyl)amino]benzamide hydrochloride (21.8 g), 17.8 g powdered anhydrous Na₂CO₃, 11.9 g 4-hydroxy-4-phenylpiperidine, and 250 ml butanol were refluxed for 6 hours, the mixture cooled and an equal volume of CHCl₃ added. The mixture was filtered and the filtrate concentrated to dryness on the rotovap. The residue was dissolved in toluene and the tolune soln washed with water, dried, and concentrated to dryness. The residue was dissolved in 350 ml ether containing 15 ml isopropanol and acidified with dry HCl to give 31 g product (dihydrochloride).

Step 5-2-Benzyl-(2-[4-propionoxy-4-phenylpiperidyl]ethyl)amino]benzamide

2-Benzyl-(2-4-hydroxy-4-phenylpiperidyl]ethyl)amino]benzamide dihydrochloride (25 g) and 140 ml propionic anhydride were heated at 78° for 6 hrs, left overnight at room temp and concentrated on the rotovap. Water (250 ml) was added to the residue and the mixture made basic with 10% NaOH and extracted with ether. The ether was washed and dried and the soln chromatographed on silica to give 12.5 g product. This was recrystallized twice from ether, then from isopropyl ether and finally from ether to give 7.65 g, m.77–87.

|  | C | H | N |  |
|---|---|---|---|---|
| Calcd | 73.48 | 7.75 | 7.98 | (corrected for 7.69% ethyl ether) |

-continued

| | C | H | N |
|---|---|---|---|
| Found | 73.47 | 7.49 | 8.01 |

Step 6-2-(2-[4-Propionoxy-4-phenylpiperidyl]ethylamino)-benzamide.

2-Benzyl-(2-[4-propionoxy-4-phenylpiperidyl]ethylamino)-benzamide (1 g) in 25 ml dimethylformamide was reduced catalytically with 5% Pd/C. The catalyst was filtered and the filtrate diluted with 100 ml water to give 0.6 g solid. This was combined with product from another batch and chromatographed on silica to give 1.2 g solid which was recrystallized twice from isopropanol to give 0.6 g, m.118–20.5.

| | C | H | N |
|---|---|---|---|
| Calcd | 69.85 | 7.39 | 10.62 |
| Found | 70.10 | 7.13 | 10.50 |

EXAMPLE XXVIII

Preparation of 2-[Benzyl-(2-[4-propionoxy-4-phenylpiperidyl]ethyl)amino]-N-methyl-benzamide (828-363)

The title compound was prepared in accordance with the technique of Steps 1 to 5 of Example XXVII, substituting amino-N-methyl-benzamide for 2-aminobenzamide.

EXAMPLE XXIX

Preparation of 2-[2-(4-Propionoxy-4-phenylpiperidyl)ethylamino]-N-methyl benzamide (828-369)

The title compound was prepared in accordance with the technique of Example XXVII, subsituting 2-amino-N-methyl-benzamide for 2-aminobenzamide.

EXAMPLE XXX

Preparation of 2-[2-(4-phenyl-1-piperidyl)ethylamino]benzamide (751-393)

A mixture of 6.1 g 4-phenyl-1-(2-chloroethyl)piperidine hydrochloride (prepared) from 4-phenylpiperidine by treatment with ethylene oxide to give the 1-(2-hydroxyethyl derviative followed by chlorination with thionyl chloride.), 4.0 g 2-aminobenzamide, 100 ml dry diglyme, and 11.7 ml triethylamine was heated 24 hrs at 150°, cooled to room temp and the solid filtered and washed with diglyme. The filter was concentrated to dryness under vac to give 10 g of an oil which was chromatographed on silica to give 3.3 g product. Two recrystallizations from 95% alcohol gave 0.8 g, m.132–4.5.

| | C | H | N |
|---|---|---|---|
| Calcd | 74.27 | 7.79 | 12.99 |
| Found | 74.48 | 8.09 | 13.06 |

EXAMPLE XXXI

2-[N-$\beta$-(1-Piperidinoethyl)amino]benzamide. (730-307)

A mixture of 54.4 g 2-aminobenzamide and 36.8 g N-(2-chloroethyl)-piperidine hydrochloride was heated 24 hours at 130–40°, cooled to room temperature, the mixture stirred with water and filtered. The filtrate was made basic with 50% NaOH and the solid filtered to give 80 g crude product. This was refluxed ½ hour with 4 liters of benzene, filtered, and cooled to room temperature to give 18.6 g which was dissolved in 800 ml acetone, treated with charcoal and the solution concentrated to 300 ml to give 14.2 g product, m.157–8.

| | C | H | N |
|---|---|---|---|
| Calcd. | 68.02 | 8.50 | 17.00 |
| Found | 68.20 | 8.76 | 17.13 |

EXAMPLE XXXII

Preparation of 2-[Methyl-2-(4-phenyl-1-piperazinyl)ethylamino]benzamide (740-274)

Step 1. 1-(2-Hydroxypropyl)-4-phenylpiperazine hydrochloride N-Phenylpiperazine (130 g.) was dissolved in 200 ml methanol and the solution cooled to 0–10°. Propylene oxide (62 ml.) was added over 5 minutes at a temperature under 10°. After the addition the cooling bath was removed. The reaction was allowed to warm to a maximum of 30°. When the reaction temperature stopped rising the solution was refluxed for 1½ hours and then cooled. A solution of 1 mole HCl gas in 100 ml. methanol was added gradually followed by 300 ml. ether. The solid was filtered, washed with methanol-ether, then with ether to give 170 g., m.201–5°.

Step 2. 1-(2-Chloropropyl)-4-phenylpiperazine dihydrochloride 1-(2-Hydroxypropyl)-4-phenylpiperazine hydrochloride (155 g.) was suspended in 1200 ml. dry chloroform and 87.5 ml. thionyl chloride added dropwise. The mixture was refluxed 2½ hrs., and cooled overnight at room temperature. The solid was filtered, washed with chloroform, then with ether, and dried to give 175 g., m.216–18°.

Step 3. 2-[1-Methyl-2-(4-phenyl-1-piperazinyl)ethylamino]benzamide hydrochloride A mixture of 75 g. 2-aminobenzamide, 138 g. sodium acetate, 174 g. 1-(2-chloropropyl)-4-phenylpiperazine dihydrochloride, and 455 ml. water was refluxed 4 hours and left overnight at room temperature. Chloroform (200 ml.) was added, the mixture stirred, then filtered. The solid was washed with chloroform which dissolved most of it. The chloroform was separated, the aqueous layer washed with chloroform. The combined chloroform extracts were washed with water, dried, and concentrated to dryness. The residue was recrystallized from 1800 ml. ethanol to give 26.3 g., m.197–8. A 3rd recrystallization from 1600 ml. ethanol gave 22.4 g. m.196–8.5. A 10 g. portion of this was suspended in 100 ml. 95% ethanol, heated to near reflux and 15 ml. 10% hydrochloric acid added. The mixture was cooled with stirring and the solid filtered, washed with ethanol, and dried over P$_2$O$_5$ under vacuum to give 10.8 g., m.274-81(dec.)

|        | C     | H    | Cl   | N     |
|--------|-------|------|------|-------|
| Calcd. | 64.07 | 7.26 | 9.46 | 14.94 |
| Found  | 63.94 | 7.45 | 9.58 | 14.96 |

PHARMACOLOGICAL ACTIVITY OF COMPOUNDS OF THIS INVENTION

The compounds of this invention, when administered to several species of experimental animals by various routes, have been found to possess effective analgesic activity and can antagonize strong narcotic analgesics as indicated by use of conventional testing methods. These compounds are characterized further by a very low order of toxicity in experimental animals and appear to be substantially non-addicting. In addition to the primary analgesic activity these compounds possess other pharmacological effects of potential utility at higher dose levels than those required for analgesia, but within an adequate margin of safety for consideration of therapeutic application. Among these other pharmacological properties are tranquilizing activity, hypothermic activity, anticonvulsant activity, antihistaminic activity, and In some cases, suspensions of the test compound as the base were used, and in others, solutions and suspensions of the hydrochloride salt were used in testing for analgesia and other pharmacological properties. Different lots of the compounds prepared as disclosed have not been found to display significant differences.

ANALGESICS

Established methods were employed for demonstrating analgesia and consisted of the following: A modification of the Eddy and Leimbach (Exp. Biol & Med. 95:729, (1957)) mouse hot plate test was used. The end point of this test is the time required for animals, pretreated with various dose levels of the test compounds or standard analgesics such as morphine or codeine, to react to the heat stimulus by raising or licking the feet or by jumping. The dose of compound or standard which results in significant analgesic effect in 50% of the animals is calculated on the basis of the number showing response times exceeding the mean control time by two seconds or more. Ten animals are used for each dose level.

In addition to the hot plate method, the writing test described by Sigmund et al., Soc. Exp. Biol. and Med. 95:729 (1957) has been applied in both rats and mice as further indication of analgesics. This method has been reported to be of value in detecting activity of narcotic antagonist analgesics which sometimes do not exhibit activity with use of other conventional methods. The stimulus of intraperitoneal injection of phenylbenzoquinone results in a writhing syndrome characterized by periodic twisting and stretching of the body with extension of the hind legs. Frequency of writhing has been shown to be reduced or prevented by prior administration of narcotic and non-narcotic analgesics. A test compound is considered to have analgesic properties if, by prior administration, it is able to reduce significantly the number of writhes from that obtained by a group receiving vehicle alone. The dose of compound protecting 50% of the animals is determined and expressed as the ED$_{50}$. Ten animals are used at each dose level.

NARCOTIC ANTAGONISTS

Certain compounds have the ability to antagonize the activity of strong narcotic analgesics in animals, whereas when tested by conventional methods in mice and rats little or no analgesia can be demonstrated. Some of these compounds have been shown to be very effective analgesics in man. The compounds of this invention were tested for their ability to antagonize narcotic analgesics by two different tests. When oxymorphone, a morphine derivative, is administered to mice, pupil dilation occurs. It has been demonstrated in our laboratory that narcotic antagonists are able to reduce this mydriatic response significantly if administered prior to oxymorphone whereas narcotic agents such as morphine and codeine cause no change or an increase in the pupil size. Another test used for narcotic antagonist activity was published by Harris & Pearson. This test is modification of the D'Amour & Smith method.

In the original method the time required for rats to flick their tails following application of a heat stimulus is taken as a measure of analgesic potency. As modified by Harris & Pearson the drug being tested for narcotic antagonism is administered prior to the morphine. An antagonist reduces or prevents analgesia from the morphine. Both of the methods described have been utilized to test the narcotic antagonist characteristics of the compounds of the examples.

LOCAL ANESTHETIC ACTIVITY

An effective local anesthetic causes a blockade of the nerves of the lower leg and foot causing the animal, when permitted to walk, to do so flatfooted, rather than its normal habit, up on its toes. Alternatively an effective local anesthetic, by the sciatic block method, can cause the leg to be dragged by the animal when walking so long as effective sciatic block persists. Toxic agents may effect the same apparent results, but the blockade effected by toxic agents is irreversible. However, in contrast to toxic agents, an effective local anesthetic permits recovery of the use of the leg and foot after a period of time.

The mice used in the sciatic block test were placed in a holder with their hind limbs extended. A quantity of the test compound (e.g. 0.05 ml) was injected into the area surrounding the sciatic nerve at the juncture of the two major leg muscles. Effective local anesthetic activity is indicated in Table IV ("Pos."--meaning that the blockade did take place and that the leg and foot returned to normal after a time.)

ANALGESIC ACTIVITY

Results:

Tables I and IV summarize the results obtained with the compounds of this invention when tested for analgesic activity and provides a comparison with morphine and codeine.

For example, compound 740-222 (the compound of Example II) is more active by the oral than the parenteral route, an unusual characteristic. Analgesic activity of this compound is of the same order as codeine and slightly less than morphine by the oral route utilizing the hot plate test in mice. By the writhing test in mice this compound has approximately one third the activity of morphine and is about 1½ times as active as codeine. The writhing syndrome is also 50% blocked in rats pretreated with 10 mg/Kg of 740-222 by the oral route. The compound produces a slight antagonism of oxymorphone induced mydriasis in mice by the intraperiteneal route only. It was not effective by the subcutaneous route in antagonizing morphine analgesia in rats. This may have been due to its low solubility, causing a poor absorption by this route.

The acute toxicity of compound 740-222 by all routes tested in mice is greater than 1 gm/kg body weight which is substantially above effective analgesic doses. The therapeutic index i.e. the relationship of the lethal dose to the effective dose for this compound by the oral route is greater than 300. The highest dose that can be administered without gross evidence of sedation is approximately 10 times that necessary to produce effective analgesia.

Table I also indicates the results of testing compound 730-372 (the compound of Example I) for analgesic activity. This compound is more active by the parenteral routes than by the oral route. By the hot plate and writhing tests 730-372 has been found to be approximately equivalent to or slightly more active than morphine. It was effective in antagonizing oxymorphone induced mydriasis and at lower dose levels antagonism of morphine analgesia was observed in rats. These data support the contention that this compound is a narcotic antagonist analgesic.

TABLE II-continued

| | | | |
|---|---|---|---|
| Cat | p.o. | >1,000* | |
| | i.p. | >1,000* | >1000* |

* = preliminary result
Toxicities have only been run with male animals to date.
Studies using females will begin shortly.

TRANQUILIZER ACTIVITY

The tranquil sedation has been observed in mice, rats, cats and monkeys following administration of these compounds in doses exceeding those that are required for analgesia. In addition further indirect evidence for tranquilizer activity has been obtained by application of a method described by Witkin et al., J. Pharmacol, and Exp. Ther. 126:330 (1959)

This test is based upon observations that the pinna reflex of the mouse is blocked at relatively low doses of major tranquilizer drugs whereas very high doses are needed to block the corneal reflex. A ratio of $ED_{50}$ corneal/$ED_{50}$ pinna exceeding unity is taken as evidence of tranquilizer type action. The compound 740-222 (the compound of Example II) displayed a ratio of greater than 10 and is therefore classified as possessing tranquilizer activity. Preliminary results with compound 730-372 (the compound of Example I) indicate a ratio of approximately 0.5 which is within the range of ratios expected with sedatives (0.3 to 0.7) and ap-

TABLE I

| | | Analgesic Activity of 740-222 & 730-372 | | | | | | |
|---|---|---|---|---|---|---|---|---|
| | | | | Writhing | HNSD./$ED_{50}$ | | $LD_{50}$/$ED_{50}$ | |
| Compound | Species | Route | Hot Plate $ED_{50}$ | $ED_{50}$ | H.P. | Writhing | H.P. | Writhing |
| 740-222 | Mouse | p.o. | 20 | 11 | 5 | 9 | >50 | >91 |
| | Mouse | i.p. | 52 | — | 3.4 | — | >17 | — |
| | Mouse | s.c. | >562 | — | — | — | — | — |
| | Rat | p.o. | | ≃14 | | 7.1 | | 71 |
| | D'Amour Smith | Rat Tail Flick p.o. $ED_{50}$ | >100 mg/kg | | | | | |
| 730-372 | Mouse | p.o. | 3.0 | 2.9 | 1.9 | 1.9 | >330 | >340 |
| | Mouse | i.p. | 1.5 | | 1.2 | — | 670 | — |
| | Mouse | s.c. | 4.1 | 1.6 | 2.4 | 6.3 | >240 | >620 |
| | Rat | Sub. cut | | 2.5 | | 2.0 | | 400 |
| | D'Amour Smith | Rat Tail Flick Sub. cut. $ED_{50}$ | >18 mg/kg | | | | | |
| Morphine | Mouse | p.o. | 14 | 3 | 4.0 | 19.0 | 570 | 267 |
| | Mouse | i.p. | 2.5 | — | 4.0 | — | 100 | — |
| | | Rat Tail Flick Sub. cut. $ED_{50}$ | | 15 mg/kg | | | | |
| Codeine | Mouse | p.o. | 20 | 17 | 5.0 | 5.9 | 27 | 32 |
| | Mouse | i.p | 12 | — | 2.6 | — | 8.7 | — |

HNSD = highest dose which can be administered without development of any gross symptoms such as depression, convulsions etc.

The acute toxicity of compound 730-372 (as indicated by the $LD_{50}$) is shown in Table II to be greater than 800 to 1000 mg/kg body weight when assessed in mice by various routes of administration. The therapeutic index is greater than 300.

TABLE II

| | | ACUTE TOXICITIES | | | |
|---|---|---|---|---|---|
| | | 740-722 | 730-372A | | |
| | Route of | $LD_{50}$ | $LD_{50}$ | Morphine | Codeine |
| | Adminis- | (48 hr) | (48 hr) | $LD_{50}$ | $LD_{50}$ |
| Species | tration | mg/kg | mg/kg | (48 hr) | (48 hr) |
| Mouse | p.o. | >10,000 | >1000 | ≃800 | 540 |
| | i.p. | >2,500 | >1000 | 250 | 104 |
| | i.v. | — | 50 | | |
| | s.c. | >1,000 | >1000 | — | — |
| Rat | p.o. | — | — | | |
| | s.c. | >1,000* | >1000* | | |
| | i.p. | — | — | | |

NOTE:
Compounds were administered in 2% clearjel as a suspension except in the case of i.v. 730-372A which was a solution (5mg/ml) in distilled water. Exact $LD_{50}$ values could not be obtained due to low compound solubility limiting the concentration which could be administered.

proaches the range of ratios for minor tranquilizers with central muscle relaxant activity.

These compounds have been tested for antihistaminic properties utilizing segments of isolated guinea pig ileum suspended in Kreb Ringer solution maintained at 37° C. with aeration of a 95% $O_2$+5% $CO_2$ mixture. Contractions were elicited by histamine phosphate. The concentration of compound required to block these contractions when added to the tissue bath prior to introduction of histamine is taken as evidence for antihistaminic action. Table III reveals that 740-222 has about the same activity as the standard antihistaminic diphenhydramine and compound 730-372 is about half as active as the standard.

HYPOTHERMIC EFFECT

Rectal temperatures were recorded periodically in mice following administration of 740-222 by oral route. Codeine was used for comparison. This compound effectively reduced body temperature in normal mice. Compound 730-372 was also effective in this respect.

ANTICONVULSANT ACTIVITY

Administration of pentylentetrazol (Metrazol) to mice resulted in convulsive seizures which could be blocked or reduced effectively by anticonvulsant agents, such as phenobarbital. Compound 740-222 administered by the oral route was able to antagonize these metrazol induced convulsions in mice. Compound 730-372 was not effective by the subcutaneous route in this respect.

GASTROINTESTINAL MOTILITY SUPPRESSION

The opium alkaloids are the most effective agents for causing constipation or treating diarrhea. It has been found that 720-222 is effective in suppressing intestinal motility in mice. The method used was a modification of that described by Brittain & Collier (J. Phsiol. 141:14p, (1958). In this method the length of intestine traversed by an orally administered suspension of charcoal is measured. Compounds which inhibit motility effectively, reduce the percentage of the small intestine traversed. 740-222 reduces gut motility as indicated by a comparison with codeine. This effect is less important with compound 730-372.

Unless otherwise indicated, the test compounds of Table IV are the title compounds of the Examples hereof to which reference is made in Table IV.

TABLE III

Activity of 740-222 and 730-372 on isolated guinea pig ileum screen

| Compound | Amount in micrograms to produce a 50% block of: | |
|---|---|---|
| | Acetylcholine | Histamine |
| 740-222 | 1000 | 0.5 |
| | 126 | 0.8 |
| Diphenhydramine | 6 | 0.4 |

Table IV

| EXAMPLE | TOXICITY HNSD[1] I.P. | TOXICITY LD$_{50}$[2] I.P.[4] | ANALGESIA PHENYLBENZOQUINONE WRITHING ED$_{50}$ P.O.[3] mg/kg | ANALGESIA PHENYLBENZOQUINONE WRITHING ED$_{50}$ S.C.[5] mg/kg | MOUSE TAIL STIMULATION ED$_{50}$ S.C. mg/kg | LOCAL ANESTHESIA SCIATIC BLOCK | NARCOTIC ANTAGONISM I.P. |
|---|---|---|---|---|---|---|---|
| I | 2 | 800 | 4 | 1 | — | — | Positive |
| VII | 3 | 300 | 40 | 50 | — | Positive | Positive |
| XII | 300 | 300 | 100 | 100 | — | Positive | Negative |
| XIV | 10 | 300 | 30 | 1 | — | Positive | Positive |
| XV | 3 | 200 | 20 | 2 | — | Positive | Positive |
| XVI | 10 | 250 | 25 | 1 | 30 | — | Positive |
| XVII | 10 | 70 | 80 | 5 | — | Positive | Negative |
| XVIII | 1 | 300 | 7 | 0.3 | — | — | Positive |
| XIX | — | 300* | 31.7 | 0.75 | — | — | Negative |
| XX | 10 | 100 | 100 | 100 | — | — | Positive |
| XXI | 10 | 200 | 100 | 10 | — | Positive | Positive |
| XXII | 0.3 | 300 | 1 | 0.6 | — | Negative | Positive |
| XXIV | 30 | 300 | 100 | 10 | — | — | Negative |
| XXVI | 3 | 200 | 100 | 60 | — | Positive | Negative |
| XXVII (Step 4 Title Compound) | 10 | 60 | 100 | 7 | — | — | Negative |
| XXVII (Step 5 Title Compoud) | 3 | 100 | 10 | 1 | — | — | Negative |
| XXVII | 0.1 | 60 | 20 | 0.06 | 0.03 | — | Negative |
| XXVIII | — | 250* | 9.3 | 0.2 | — | — | Negative |
| XXIX | — | 16* | 20.2 | 0.09 | — | — | Negative |
| XXX | 10 | 200 | 100 | 3 | — | Positive | Positive |
| XXXI | 10 | 40 | 20 | — | — | — | Positive |
| XXXII | 3 | 300 | 3 | 30 | — | — | Negative |
| Controls: Morphine | 10 | 380 | 2.6 | 0.5 | 1.5 | Negative | Negative |
| (Controls) Meperidine | 30 | 130 | 18.0 | 1.7 | 1.8 | Positive | Negative |
| Pentazocine | 30 | 140 | 56 | 2.0 | — | Positive | Positive |

[1]HNSD : Highest Nonnsymptomatic Dose
[2]LD$_{50}$ : Median Lethal Dose
[3]P.O. : Oral
[4]I.P. : Intraperitoneal
[5]S.C. : Subcutaneous
*Oral

What is claimed is:

1. A member of the group consisting of (a) a compound having the formula:

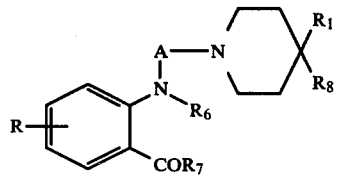

wherein:
R is H, lower alkyl, hydroxy, lower alkoxy, halogen, amino or —NHCHO;
A is $(CH_2)_n$, where n is 1–5, or branched chain alkyl of 3–5 carbons;
$R_1$ is phenyl;
$R_6$ is H, lower alkyl, lower alkanoyl, benzoyl, benzyl or benzyl substituted in the ring with $NH_2$, OH, $OCH_3$ or Cl;
$R_7$ is —$NH_2$, —NH-lower alkyl or —N=(disubstituted with lower alkyl);
$R_8$ is —OH or —$OCOR_9$;
$R_9$ is lower alkyl; and
(b) a pharmacologically acceptable acid addition salt thereof.

2. The compound of claim 1 wherein R is hydrogen, A is $(CH_2)_2$, $R_1$ is phenyl, $R_7$ is —$NHCH_3$, and $R_8$ is propionoxy.

3. The compound of claim 2 wherein $R_6$ is benzyl.

4. The compound of claim 2 wherein $R_6$ is hydrogen.

* * * * *